(12) United States Patent
Dobson

(10) Patent No.: US 7,868,222 B1
(45) Date of Patent: Jan. 11, 2011

(54) TRANSFECTED MOSQUITO VECTORS

(75) Inventor: Stephen L. Dobson, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 296 days.

(21) Appl. No.: 11/373,042

(22) Filed: Mar. 10, 2006

(51) Int. Cl.
*A01K 67/00* (2006.01)
*A01K 67/033* (2006.01)

(52) U.S. Cl. .............................. 800/13; 800/8
(58) Field of Classification Search ............. 800/8, 800/13
See application file for complete search history.

(56) References Cited

U.S. PATENT DOCUMENTS

| | | | |
|---|---|---|---|
| 5,627,048 | A | 5/1997 | Afanasiev et al. |
| 5,753,434 | A | 5/1998 | Ryner et al. |
| 6,503,500 | B1 | 1/2003 | Zaritsky et al. |
| 2002/0194634 | A1 | 12/2002 | Craig et al. |
| 2003/0213005 | A1 | 11/2003 | Alphey et al. |
| 2005/0120395 | A1 | 6/2005 | Burt |

OTHER PUBLICATIONS

Duron et al., 2006, Heredity, vol. 96, p. 493-500.*
Dobson et al., 2004, Heredity, vol. 93, p. 135-142.*
Dobson et al., 2002, Genetics, vol. 160, p. 1087-1094.*
Xi et al., 2005, Insect Biochemistry and Molecular Biology, vol. 35, p. 903-910.*
Dobson, S., 2005, American Journal of Tropical Medicine and Hygiene, vol. 73, No. 6, Supplement [S], pp. 348, MA 1059.*
Dobson et al., 2001, Journal of Medical Entomology, vol. 38, No. 3, p. 382-387.*
Boyle L, O'Neill SL, Robertson HM, Karr TL (1993) Interspecific and intraspecific horizontal transfer of *Wolbachia* in *Drosophila*. Science 260(5115): 1796-1799.
Braig HR, Guzman H, Tesh RB, O'Neill SL (1994) Replacement of the natural *Wolbachia* symbiont of *Drosophila simulans* with a mosquito counterpart. Nature 367(6462): 453-455.
Chang NW, Wade MJ (1996) An improved microinjection protocol for the transfer of *Wolbachia pipientis* between infected and uninfected strains of the flour beetle *Tribolium confusum*. Canadian Journal of Microbiology 42(7): 711-714.
Fujii Y, Kageyama D, Hoshizaki S, Ishikawa H, Sasaki T (2001) Transfection of *Wolbachia* in Lepidoptera: the feminizer of the adzuki bean borer *Ostrinia scapulalis* causes male killing in the Mediterranean flour moth *Ephestia kuehniella*. Proceedings of the Royal Society of London Series B-Biological Sciences 268(1469): 855-859.
Jager CR, Pintureau B, Grenier S, Heddi A (1997) Detection of *Wolbachia* within *Trichogrammatidae* species using *FtsZ*-PCR, and horizontal transfer by microinjection. Proceedings of the Section Experimental and Applied Entomology of the Netherlands Entomological Society 8: 47-52.
van Meer MMM, Stouthamer R (1999) Cross-order transfer of *Wolbachia* from *Muscidifurax uniraptor* (Hymenoptera : Pteromalidae) to *Drosophila simulans* (Diptera : Drosophilidae). Heredity 82: 163-169.
van Meer MMM, Witteveldt J, Stouthamer R (1999) Development of a microinjection protocol for the parasitoid *Nasonia vitripennis*. Entomologia Experimentalis et Applicata 93(3): 325-329.
Kang L, Ma X, Cai L, Liao S, Sun L et al. (2003) Superinfection of *Laodelphax striatellus* with *Wolbachia* from *Drosophila simulans*. Heredity 90(1): 71-76.
Zabalou S, Riegler M, Theodorakopoulou M, Stauffer C, Savakis C et al. (2004) *Wolbachia*-induced cytoplasmic incompatibility as a means for insect pest population control. Proceedings of the National Academy of Sciences of the United States of America 101(42): 15042-15045.
Russell JA, Moran NA (2005) Horizontal transfer of bacterial symbionts: Heritability and fitness effects in a novel aphid host. Applied and Environmental Microbiology 71(12): 7987-7994.
Xi Z, Dean JL, Khoo C, Dobson SL (2005) Generation of a novel *Wolbachia* infection in *Aedes albopictus* (Asian tiger mosquito) via embryonic microinjection. Insect Biochemistry and Molecular Biology 35(8): 903-910.
Xi Z, Dobson SL (2005) Characterization of *Wolbachia* transfection efficiency by using microinjection of embryonic cytoplasm and embryo homogenate. Applied and environmental microbiology 71(6): 3199-3204.
Xi Z, Khoo CCH, Dobson SL (2006) Interspecific transfer of *Wolbachia* into the mosquito disease vector *Aedes albopictus*. Proceedings of the Royal Society of London Series B-Biological Sciences 273: 1317-1322.
Xi Z, Khoo CCH, Dobson SL (2005) *Wolbachia* Establishment and Invasion in an *Aedes aegypti*. Laboratory Population. Science 310: 326-328.

* cited by examiner

*Primary Examiner*—Shin-Lin Chen
(74) *Attorney, Agent, or Firm*—Stites & Harbison PLLC; Stephen J. Weyer; Mandy Wilson Decker

(57) ABSTRACT

A method is provided for producing an artificial infection in a Culicidae (mosquito) species. The mosquitoes include species within the subfamilies Culicinae and Anophelinae, and the species include *Aedes albopictus, Aedes aegypti* and *Aedes polynesiensis* infected with a *Wolbachia* infection. The infection may be a strain of *Wolbachia* which does not normally or naturally infect the selected mosquito species. The artificially infected *Aedes* mosquito can be introduced into a mosquito population to control the reproduction capability of the population by introducing an incompatible *Wolbachia* infection. The present method can be used as a novel means to limit mosquito-borne pathogens and thus control or prevent mosquito-borne diseases such as dengue, lymphatic filariasis, etc.

7 Claims, 10 Drawing Sheets

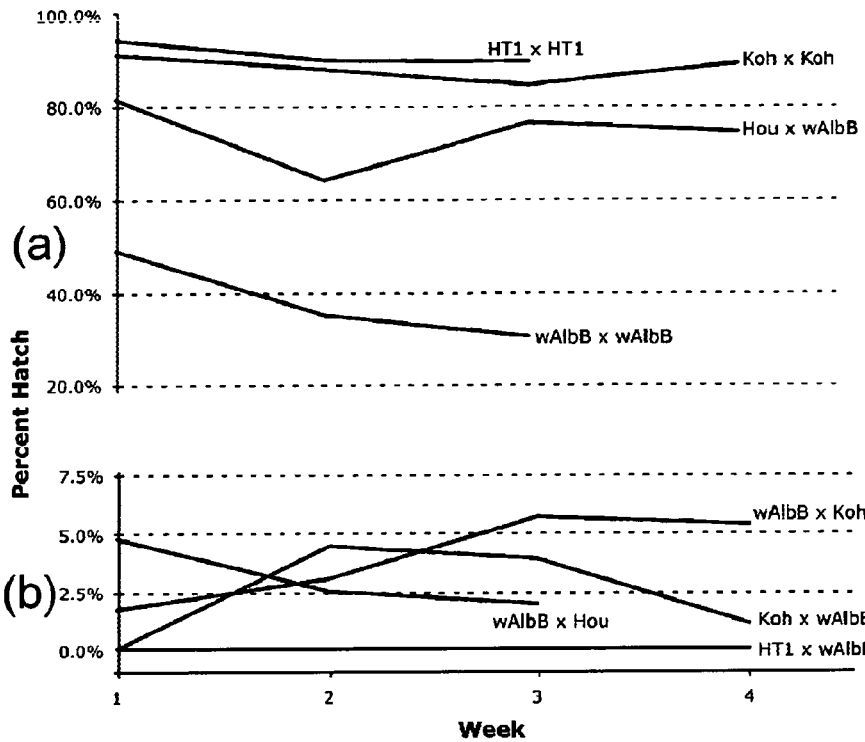
FIGURE 4 (a)
FIGURE 4 (b)
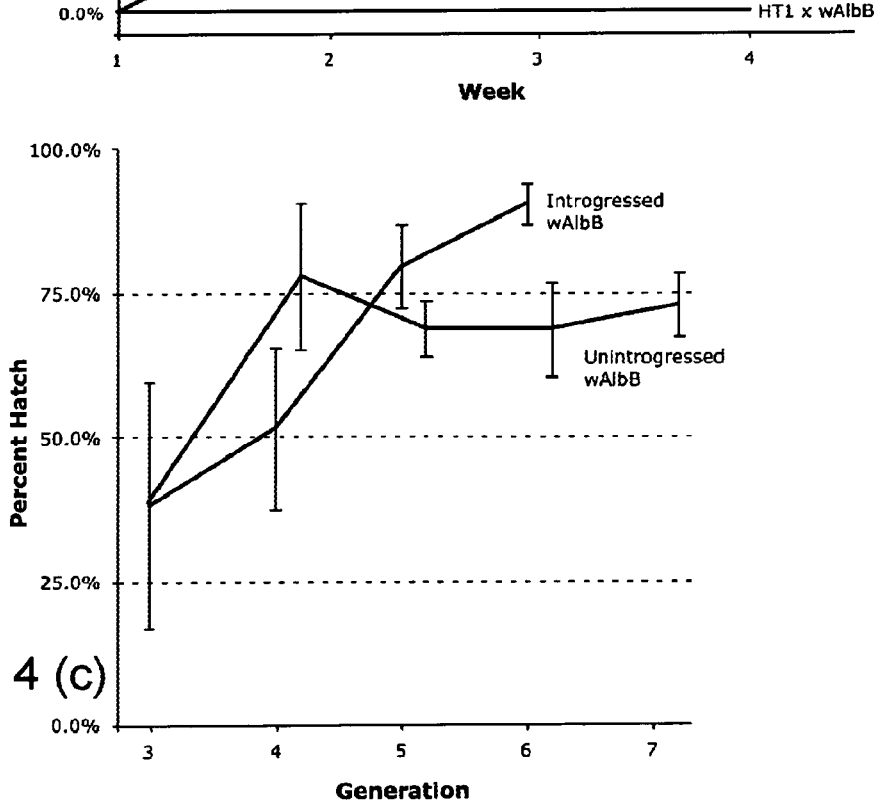
FIGURE 4 (c)

TRANSFECTED MOSQUITO VECTORS

FIELD OF THE INVENTION

The present invention relates to transfected mosquito vectors and in particular Diptera: Culicidae (mosquito) vectors transfected with *Wolbachia*.

BACKGROUND OF THE INVENTION

Malaria, dengue and dengue haemorrhagic fever, WNV and other encephalites, human African trypanosomiasis (HAT), human filariasis, dog heartworm and other pathogens important to animals are on the increase. Although vector control methods are available to interrupt transmission of these diseases, their effectiveness has been limited by logistic problems, development of resistance to insecticides, regulatory restrictions related to environmental concerns and high cost. Novel, sustainable approaches to control are urgently needed.

Recent molecular advances in the understanding of vector genetics and vector-parasite/virus relationships have provided novel tools for the study of disease transmission. Among these are germ-line transformation of mosquitoes, detailed genetic and physical maps, molecular genetic markers for the identification of cryptic species, detection of pathogens in vectors, gene flow studies, detection of insecticide resistance, and the complete genome of *Anopheles gambiae* as well as collections of expressed sequence tags (ESTs) from a variety of disease vectors. However, much work remains to be done to identify, at the molecular level, the role of insect vectors in disease transmission, and the mechanisms for interfering with vector competence.

Insect vectors of disease constitute a major threat to human and animal health. Malaria, the most prevalent of the mosquito-born diseases, afflicts 300-400 million people annually, of which about 1% die from the disease. Malaria and other vector-borne diseases are increasing in the world today for a variety of reasons, including vector resistance to pesticides, parasite resistance to drugs, more movement by people, climatic changes, etc. Warm areas of the United States, such as Arizona, with its proximity to the reservoirs of disease in Central America, are especially vulnerable to spread of vector-borne diseases. Attempts to lessen the impact of malaria and the other insect-born diseases require extensive knowledge of the vector insect, of the causative agent, and of the interaction between vector and parasite or vector and virus.

The primary indirect effect of medical and veterinary insects is disease transmission. Indeed, disease transmission is more important than any other effect produced by medical and veterinary pests. Underlying the relationship of arthropods to disease requires consideration of many concepts and much terminology.

Organisms that produce disease are called pathogens and disease itself is a stress condition produced by the effects of a pathogen on a susceptible host. Arthropods capable of transmitting pathogens are called vectors. Some diseases may depend on only a single host and a vector; however, other diseases may include multiple host species, and even multiple vectors. In many of these instances, an organism that maintains the infective agent (the pathogen source) when active transmission does not occur is termed a reservoir. For example, the reservoir for malaria is human populations, with transmission occurring when a mosquito feeds on an infected individual and later feeds on an uninfected individual.

Fundamentally, disease is a manifestation of interactions between host and pathogen. An array of environmental and physiological factors may influence these interactions. Many aspects of insect behavior and life history are important in disease transmission, especially those relating to relationships between vectors and hosts. Generally, the closer the association between vector and host, the greater the suitability of the vector to transmit the disease.

*Aedes aegypti*, *Aedes albopictus*, and *Aedes polynesiensis* are medically important vectors of pathogens including dengue, yellow fever, filariasis, dog heartworm, West Nile and other encephalites. The transfected strains that have been generated may be used to suppress, eliminate or replace naturally occurring vector populations.

*Wolbachia* is a genus of obligate, intracellular, maternally inherited bacteria that occur in many insect species. Cytoplasmic incompatibility (CI) is one of several reproductive manipulations caused by *Wolbachia*. CI occurs in matings between individuals that differ in their *Wolbachia* infection type and results in early embryonic death. The CI mechanism is unknown as disclosed by Charlat, S., Calmet, C., Mercot, H., 2001 "On the mod resc model and the evolution of *Wolbachia* compatibility types", Genetics 159, 1415-1422, (hereinafter Charlat 2001); Poinsot et al. "On the mechanism of *Wolbachia*-induced cytoplasmic incompatibility: confronting the models with the facts", Bioessays 25, 259-265, 2003; and Dobson, S. L., Rattanadechekul, W., Marsland, E. J., "Fitness advantage and cytoplasmic incompatibility in *Wolbachia* single and super-infected *Aedes albopictus*", Heredity 93, 135-142, 2004 (hereinafter Dobson 2004). *Wolbachia* in the male acts to 'modify' the sperm, such that karyogamy failure occurs following fertilization, resulting in embryo death. If the female (and resulting fertilized egg) have the same *Wolbachia* type as her mate, *Wolbachia* acts to 'rescue' the modification, resulting in normal embryo development. Thus, matings between uninfected females and infected males are incompatible, but the reciprocal cross is compatible (unidirectional CI). Unidirectional CI provides *Wolbachia*-infected females with a reproductive advantage relative to uninfected females, promoting the spread of maternally inherited *Wolbachia* into uninfected host populations. The ability to spread into host populations has led to the proposed use of *Wolbachia* in population replacement strategies. Specifically, a desired transgene that is linked to *Wolbachia* could be 'seeded' into a mosquito disease vector population. The *Wolbachia* infection would then serve as a vehicle, driving the linked transgene into the targeted population. Additionally, the introduced *Wolbachia* infection may directly have a desired impact on the targeted insect population (i.e., genetic modification of *Wolbachia* strain not required). Bidirectional CI can occur when two or more *Wolbachia* types infect the same host population. An example is provided by the parasitoid wasp *Nasonia vitripennis*. Crosses between *N. vitripennis* strains that are infected with divergent *Wolbachia* types (A type or B type) result in incompatibility in both cross directions. Theory predicts that bidirectionally incompatible *Wolbachia* types cannot persist within a panmictic host population as taught by Rousset, F., Raymond, M., Kjellberg, F., 1991, "Cytoplasmic incompatibilities in the mosquito *culex pipiens*: how to explain a cytotype polymorphism?", J. Evol. Biol. 4, 69-81, (hereinafter Rousset 1991); and Dobson, S. L, Fox, C. W., Jiggins F. M., 2002, "The effect of *Wolbachia*-induced cytoplasmic incompatibility on host population size in natural and manipulated systems", Proc. R. Soc. London B Biol. Sci. 269, 437-445, (hereinafter Dobson 2002), both incorporated herein by reference. Bidirectional CI causes a 'battle' between the *Wolbachia* types, resulting in the elimination of infections until only one *Wolbachia* type predominates. The host population is a victim during this battle, as bidirectional incompatibility sterilizes many matings. The CI-induced suppression of the host population is transient however, lasting only until one *Wolbachia* infection type dominates the host population. Therefore, known examples of bidirectional CI have been either artificially generated or isolated from allopatric populations.

Vector population suppression and elimination strategies are based upon artificially prolonging the bidirectional CI battle as taught by Dobson 2002. In a prior field test of the strategy, releases of bidirectionally incompatible males successfully eliminated a *Culex* mosquito vector population from a village in Burma (Myanmar) as provided in Laven, H. 1967. "Eradication of *Culex* pipiens fatigans through cytoplasmic incompatibility". Nature 216: 383-384. However, the availability of naturally occurring bidirectionally incompatible strains that permitted the *Culex* strategy remains unique among mosquitoes. Therefore, the use of the suppression/elimination strategy in additional mosquito vector populations requires the ability to artificially generate incompatible strains. Similarly, population replacement strategies also require an ability to generate novel infections. Although the artificial transfer of *Wolbachia* (transfection) has been successfully accomplished in other insect systems as taught by Boyle et al., "Interspecific and intraspecific horizontal transfer of *Wolbachia* in *Drosophilia*" Science 260, 1796-1799, 1993; Sasaki et al., "Interspecific transfer of *Wolbachia* between two lepidopteran insects expressing cytoplasmic incompatibility; a *Wolbachia* variant naturally infecting *Cadra cautella* causes male killing in *Ephestia kuehniella*", Genetics 162, 1313-1319, 2002; Hartmann et al., "Trans-species transfer of *Wolbachia*: micro-injection of *Wolbachia* from *Litomosoides sigmodontis* into Acanthocheilonema viteae", Parasitology 126, 503-511, 2003; and Kang et al., "Superinfection of *Laodelphax striatellus* with *Wolbachia* from *Drosophila simulans*", Heredity 90, 71-76 2003, prior efforts to generate novel infections in mosquitoes have not proven successful as shown by Sinkins, S. P., O'Neill, S. L., "*Wolbachia* as a vehicle to modify insect populations.", In: James, A.M.H.A.A. (Ed.), Insect Transgenesis: Methods and Applications, CRC Press, Boca Raton, Fla., pp. 271-287, 2000, all incorporated herein by reference.

*Aedes albopictus* (Asian tiger mosquito) is a medically important disease vector of multiple arboviruses and filaria. This mosquito is also an important invasive species, frequently spread by human transport. Since its introduction to the United States, *Ae. albopictus* has spread to become a leading biting nuisance. *Ae. albopictus* individuals are naturally co-infected with two *Wolbachia* types (wAlbA and wAlbB). This type of co-infection is known as 'superinfection' and is commonly observed in insects. Superinfection results in additive unidirectional CI: superinfected females express both the A and B rescue and are compatible with all males in the population; superinfected males express both the A and B modification and are compatible only with superinfected females.

Although a majority of *Ae. albopictus* populations are superinfected, laboratory colonies of single-infected (wAlbA) strains have been established from the islands of Koh Samui and Mauritius. Crosses demonstrate that the superinfection is unidirectionally incompatible with the wAlbA infection.

Crosses of wAlbA-infected females and super-infected males are incompatible, resulting in high embryo mortality. The males in the latter cross differ only by the wAlbB infection present in males.

*Aedes aegypti* (yellow fever mosquito) is the principle vector of dengue viruses throughout the tropical world. Without a registered vaccine or other prophylactic measures, efforts to reduce cases of dengue fever and dengue hemorrhagic fever are limited to vector control. Unfortunately, traditional mosquito control measures are not succeeding. With an estimated 100 million human cases of dengue fever every year, substantial effect is being devoted to the development of new strategies to complement existing vector control methods.

A gene drive vehicle is an important component of vector population replacement strategies, providing a mechanism for the autonomous spread of desired transgenes into the targeted population. Compared with strategies that rely on inundative releases and Mendelian inheritance, genedrive strategies would require relatively small "seedings" of transgenic individuals into a field population. Perhaps more important than increased cost efficacy, gene drive strategies can facilitate population replacement with transgenic individuals that have a lower fitness relative to the natural population.

As previously noted, Cytoplasmic incompatibility (CI), induced by naturally occurring intracellular *Wolbachia* bacteria, has attracted scientific attention as a potential vehicle for gene drive. Although CI and other forms of reproductive parasitism have made *Wolbachia* an evolutionary success, with an estimate that infections occur in ~20% of insect species, *Wolbachia* infections do not naturally occur in *A. aegypti*, raising the questions of whether *A. aegypti* can support a *Wolbachia* infection. Key parameters in *Wolbachia* infection dynamics include the intensity of CI (number of hatching eggs resulting from an incompatible cross), the maternal inheritance rates (number of uninfected progeny produced by an infected female) and mosquito fitness costs associated with the infection. These parameters also determine the infection frequency after a population replacement event, an important consideration because of the goal of population replacement is for the entire mosquito population to carry the desired genotype. The parameters also determine the rate at which the infection will invade the targeted population, an important consideration since the strategy should take place within a "human, not evolutionary, time frame." (N. Besansky, U. Notre Dame).

SUMMARY OF THE INVENTION

The present invention is directed to a novel approach for artificially infecting Culicidae (mosquito) species including the subfamilies Culicinae and Anophelinae with one or more *Wolbachia* strains. For example, Culicidae species include *Aedes albopictus*, *Aedes aegypti*, and *Aedes polynesiensis*. The *Wolbachia* strain may include both strains which naturally infect the aforementioned mosquito species as well as strains which do not naturally infect various mosquito species. The *Wolbachia* infection to be microinjected may be derived in vivo (e.g., from embryonic, immature or adult insect tissues) or may be propagated in vitro (e.g., in a tissue culture) prior to injection.

The present novel method provides for a means of generating specifically infected mosquito species as desired. The then generated infected mosquitoes can be employed to control a mosquito population by introducing a specific species infected with a specific *Wolbachia* infection into a population of mosquitoes to effect vector suppression, elimination, or replacement and to control the reproduction capability of the population.

The present invention, in one form thereof, relates to an artificial bacterial infected insect species comprising an *Aedes* mosquito species selected from the group consisting of *Aedes albopictus*, *Aedes aegypti* and *Aedes polynesiensis* infected with one or more *Wolbachia* species which does not naturally infect the selected *Aedes* mosquito species.

The present invention, in another form thereof, relates to a bacteria infected insect species, selected from the group consisting of *Aedes aegypti* and *Aedes polynesiensis*, infected with a *Wolbachia* species of bacteria.

The present invention, in another form thereof, relates to a method of infecting *Aedes* mosquito species with a bacterium comprising injecting an *Aedes* mosquito with either 1) cytoplasm from a donor species infected with *Wolbachia* or 2) cell culture comprising the *Wolbachia*, using microinjection. The *Aedes* mosquito species includes an *Aedes* mosquito species selected from the group comprising of *Aedes albopictus*, *Aedes aegypti* and *Aedes polynesiensis*.

The present invention, in another form thereof, relates to a method of mosquito population control comprising infecting an *Aedes* mosquito species with a *Wolbachia* infection by injecting an embryo from an *Aedes* mosquito with 1) cytoplasm from a donor species infected with *Wolbachia* or 2) cell culture comprising the *Wolbachia*, using microinjection and introducing *Aedes* mosquito species infected with *Wolbachia* infection into a population of mosquitoes to effect vector replacement with *Wolbachia* or population suppression or population elimination based on a *Wolbachia* incompatibility. In one further embodiment, the injected embryos are allowed to mature and reproduce to form an infected population which is then introduced into the environment population of mosquitoes.

The present invention, in another form, comprises an artificial bacteria infected mosquito species infected with one or more *Wolbachia* species which does not naturally infect the Culicidae species.

The present invention, in yet another form, comprises a method of infecting a mosquito species with a bacterium, in which the method comprises injecting an embryo from the mosquito species with 1) cytoplasm from a donor species infected with *Wolbachia* or 2) cell culture comprising the *Wolbachia*, using microinjection.

The present invention, in another form, comprises a method of infecting *Aedes polynesiensis* with a bacterium, in which the method comprises using introgression to infect the *Aedes polynesiensis* with *Wolbachia*. In one further embodiment, the *Wolbachia* is from *Ae. riversi*.

The present invention, in yet another form, comprises a method of mosquito population control, in which the method comprises infecting a mosquito species with a *Wolbachia* infection by injecting an embryo from the selected mosquito species with 1) cytoplasm from a donor species infected with *Wolbachia* or 2) cell culture comprising the *Wolbachia*, using microinjection; and introducing the mosquito species infected with a *Wolbachia* infection into a population of mosquitoes to effect vector replacement with the *Wolbachia*, or population suppression or population elimination based on *Wolbachia* incompatibility.

The present invention, in yet another form, comprises a method of mosquito population control, wherein the method comprises infecting a mosquito species with a *Wolbachia* infection using introgression to infect the mosquito with *Wolbachia*; and introducing the mosquito species infected with a *Wolbachia* infection into a population of mosquitoes to effect vector replacement with the *Wolbachia*, or population suppression or population elimination based on *Wolbachia* incompatibility.

BRIEF DESCRIPTION OF THE DRAWINGS

Further advantages and characteristics will become evident from the following description of preferred embodiments according to this invention, presented for exemplifying and non-limiting purposes with reference to the attached drawings, in which:

FIG. 4 (*a*)-FIG. 4 (*c*) are plots showing egg hatch rates wherein FIG. 4 (*a*) is the egg hatch rate compatible $G_3$ crosses, FIG. 4 (*b*) is the hatch rate in incompatible $G_3$ crosses and FIG. 4 (*c*) is the percent hatch rate in unintrogressed and introgressed wAlbB lines, where egg hatch rate measurement were either weekly (FIGS. 4 (*a*), 4 (*b*)) or once per generation (FIG. 4 (*c*));

DETAILED DESCRIPTION

The present method uses microbial pesticides in the form of *Wolbachia* for the suppression/elimination of mosquitoes and genetic strategies that reduce or block pathogen transmission by mosquitoes as a means to control mosquito populations. These strategies include vector suppression and replacement based upon intracellular *Wolbachia* bacteria, which occur naturally in many insect populations. One mechanism is cytoplasmic incompatibility (CI) through which *Wolbachia* promotes infection spread by effectively sterilizing uninfected females.

The present method employs *Wolbachia* as a vehicle to drive desired transgenes into vector populations (population replacement). The present method also provides for the suppression/elimination of mosquitoes. *Wolbachia*-based population suppression and population replacement strategies require an ability to generate artificial *Wolbachia* associations in mosquitoes.

Figure 1:
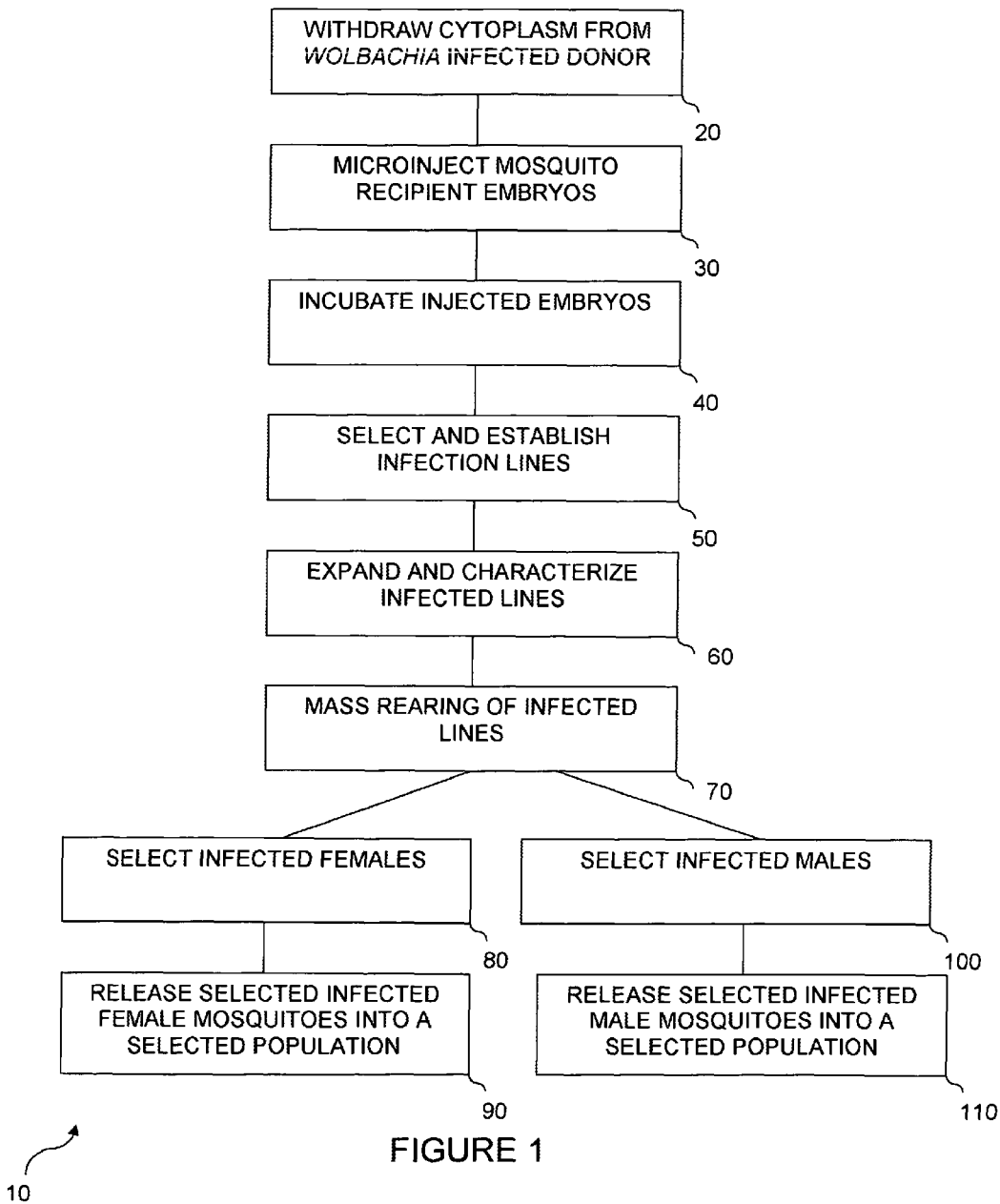
FIG. 1 is a chart schematically showing a method of transfecting mosquitoes with *Wolbachia* and using transfected mosquitoes to control mosquito populations in accordance with the present invention.

Referring now to FIG. 1, method 10 is a method for transfecting mosquitoes with one or more *Wolbachia* strains and using transfecting mosquitoes to effect vector suppressing and/or vector replacement and to control mosquito populations in accordance with one form of the present invention. When used with regard to the present invention, the terms "transfected" and "transinfected" are synonymous with one another. At step 20, cytoplasm is withdrawn from a donor infected with a *Wolbachia* infection. The donor may include a mosquito strain infected with *Wolbachia*. Alternatively, the donor can be a non-mosquito insect, which has a *Wolbachia* infection such as a *Drosophila*.

A recipient mosquito species including the subfamilies Culicinae and Anophelinae are then microinjected with the cytoplasm from the infected donor at step 30. Advantageously, a suitable microinjector or syringe is used to extract the cytoplasm from the donor infected insect (step 30). Mosquito species of genus *Aedes* (also referred to by some as its alternate or synonymous name, *Ochelerotatus*, hereinafter referred to exclusively by its *Aedes* nomenclature) include *Aedes albopictus*, *Aedes aegypti*, and *Aedes polynesiensis*. The strain of *Wolbachia* may include both *Wolbachia* which naturally infects the selected mosquito species or may be a strain of *Wolbachia* which does not infect the selected *Aedes* mosquito species naturally. For example, wAlbB, wMelPop and wRi can be introduced into *Aedes albopictus* via microinjection. wAlbB can be introduced into an *Aedes aegypti* via microinjection. wCon can be introduced into *Aedes polynesiensis* via introgression.

In an alternative to directly microinjecting the recipient mosquito with the cytoplasm from a donor species having a *Wolbachia* infection, *Wolbachia* can be grown, in vitro, in cell culture media using culture techniques known to one of ordinary skill in the art as taught by: Dobson, S. L., E. J. Marsland, Z. Veneti, K. Bourtzis, and S. L. O'Neill. 2002. Characterization of *Wolbachia* host cell range via the in vitro establishment of infections. Appl Environ Microbiol 68: 656-660. Subsequently, the in vitro grown *Wolbachia* is microinjected into the recipient mosquito embryo.

Steps 20 and 30 can be repeated to create superinfections, i.e. an mosquito infected with two *Wolbachia* strains and repeated a second time to produce a triple infection. For example, *Aedes albopictus* can be injected with both wAlbA and wAlbB to cause a superinfection and also injected with wRi to cause a triple infection by repeating steps 20 and 30. Alternatively, the donor may have a superinfection so that injection the cytoplasm from the donor into the recipient results in a superinfection in the recipient mosquito.

At step 40, the embryos are allowed to mature and at step 50, the selection and establishment of *Wolbachia* infected lines are generated. *Wolbachia* infected lines are established by screening females (G0) surviving the microinjection process for *Wolbachia* infection using a PCR assay. Lines established from females that are not infected are discarded. Lines established from females that are infected are continued by generating sublines and PCR assays as in the preceding generation.

At step 60, expansion and characterization of appropriate lines is conducted. Lines that are stably infected with *Wolbachia* are expanded by continuing to rear all offspring generated by females. As one female can generate several hundred eggs, the line can be expanded to thousands of insects within a few generations. And, at step 70, the expanded and characterized lines are reared in mass.

If one wishes to introduce the *Wolbachia* infection into a mosquito population (population replacement strategy), at step 80, infected female mosquitoes are released. Subsequently, at step 90, the selected females are released into the environment of a mosquito population to effect vector replacement.

If one wishes to affect a population suppression or population elimination, at step 100, infected male mosquitoes are selected and then subsequently released or introduced into a population of uninfected or differently infected mosquitoes in the environment at step 116. Infected males are allowed to fertilize uninfected or differently *Wolbachia* infected female mosquito eggs thereby suppressing or eliminating the population of *Aedes* mosquitoes in the selected population.

Although method 10 uses microinjection to infect mosquito embryos, which are allowed to mature, before being released into a population to control, suppress or effect vector replacement, other prior techniques can be used to artificially infect a mosquito. For example, introgression using a technique such as the method schematically shown in FIG. 10, can be used rather than microinjection to introduce a desired *Wolbachia* infection.

Figure 10:
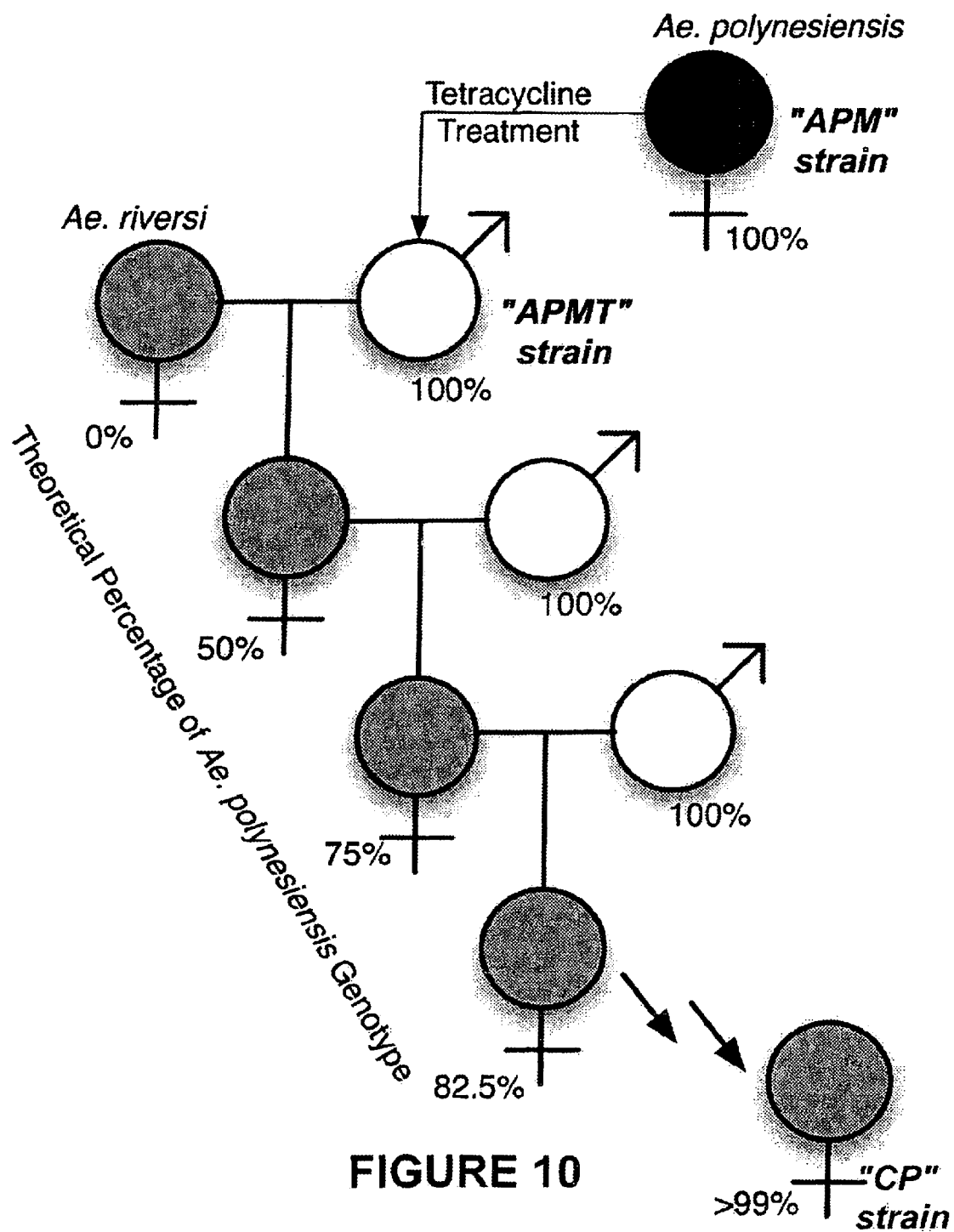
FIG. 10 is a schematic showing infection of Culicidae using introgression in accordance with the present invention.

Prior crossing experiments demonstrated that egg hatch can be induced in interspecific crosses of *Ae. polynesiensis* and *Ae. riversi* by the removal of *Wolbachia* infection, suggesting a strategy shown in FIG. 10 for the introgression of *Wolbachia* from *Ae. riversi* into *Ae. polynesiensis* in accordance with Dean, J. L., and S. L. Dobson. 2004, "Characterization of *Wolbachia* infections and interspecific crosses of *Aedes* (Stegomyia) *polynesiensis* and *Ae.* (Stegomyia) *riversi* (Diptera: Culididae)", J. Med. Entomol. 41: 894-900 (hereinafter Dean and Dobson 2004), herein incorporated by reference. The foundation of the introgression strategy is based upon generating hybrids (named 'CP$_1$') from crosses of *Wolbachia* infected *Ae. riversi* females (AR) and APMT males. The APMT strain was generated via antibiotic treatment of the naturally infected APM strain. Subsequently, crosses of CP$_1$ females with APMT males generated CP$_2$ females, which were also crossed with APMT males. Repeating this cross pattern (introgression) for multiple generations resulted in the CP strain that is predominantly *Ae. polynesiensis* genotype, but that is infected with the *Wolbachia* infection from *Ae. riversi* as shown in Dean and Dobson. 2004.

It will be apparent to one of ordinary skill in the art that the present method can be used to replace a population of mosquitoes by using the present method to infect female mosquitoes with one or more *Wolbachia* strains and introducing those infected with *Wolbachia* into a population. As the *Wolbachia* infection spreads into the field population, the infection can serve as a vehicle to carry desired transgenes into the targeted population. For example, the introduced transgene may reduce the ability of the mosquito to transmit a human pathogen. [two recent references describing transgenic population replacement strategies: Travanty E A, Adelman Z N, Franz A W, Keene K M, Beaty B J et al. (2004) Using RNA interference to develop dengue virus resistance in genetically modified *Aedes aegypti*. Insect biochemistry and molecular biology 34(7): 607-613.; Moreira L A, Wang J, Collins F H, Jacobs Lorena M (2004) Fitness of anopheline mosquitoes expressing transgenes that inhibit *Plasmodium* development. Genetics 166(3): 1337-1341.] Alternatively, the *Wolbachia* infection may have a direct effect on the mosquito population, which is desired for the reduction of vector populations or disease transmission.

The present method aids in controlling the growing burden of vector-borne disease by population suppression/elimination, in which a natural vector population is reduced or eliminated, thus reducing or eliminating the capacity of the population to transmit disease. The present method also aids in controlling vector-borne disease by population replacement, in which a natural vector population is replaced by a population with a reduced capacity for disease transmission. An important component of such strategy is the drive system, which serves to spread a desired genotype into the targeted field population. As previously noted, endosymbiotic *Wolbachia* bacteria are potential transgene drivers, but infections do not naturally occur in some important mosquito vectors, notably *Aedes aegypti*. However, using the present method, stable infections of wAlbB *Wolbachia* can be established in *A.*

*aegypti* and cause a high rate of Cytoplasmic Incompatibility (CI), and consequently the elimination of egg hatch. Laboratory cage tests demonstrate the ability of wAlbB to spread into an *A. aegypti* population after seeding of an uninfected population with infected females, reaching infection fixation within seven generations.

The present invention will now be described with regard to the following examples in the form of experiments which in no way limit the scope of the present invention.

Example 1

Transfer of *Wolbachia* from a Naturally Superinfected *Ae. albopictus* strain

This example demonstrates the use of embryonic microinjection to transfer *Wolbachia* from a naturally superinfected *Ae. albopictus* strain into an artificially generated aposymbiotic strain. The results show that transfection efforts have generated an artificial *Wolbachia* infection type (wAlbB single infection) in *Ae. albopictus*. Crossing experiments with the artificial infection show a new CI crossing type, providing the first example of bidirectional incompatibility in *Aedes* mosquito strains.

The Koh Samui strain of *Ae. albopictus* (Koh; Thailand, pre-1970) is infected with the wAlbA *Wolbachia* type in accordance with Sinkins et al., "*Wolbachia* superinfections and the expression of cytoplasmic incompatibility", Proc. R. Soc. London B Biol. Sci. 261, 325-330, 1995, (hereinafter Silkins 1995), herein incorporated by reference. The Houston strain is superinfected with both wAlbA and wAlbB *Wolbachia* types. HT1 and UjuT are uninfected strains that were artificially generated by tetracycline treatment in accordance with Otsuka and Takaoka, "Elimination of *Wolbachia pipientis* from *Aedes albopictus*", Med. Entomol. Zool. 48, 257-260, 1997; and Dobson and Rattanadechakul, "*Wolbachia* induced cytoplasmic incompatibility in single- and superinfected *Aedes albopictus* (Diptera: Culicidae)", J. Med. Entomol. 38, 382-387, 2001 (Dobson 2001), both herein incorporated by reference. Mosquitoes were maintained as previously described in accordance with Dobson et al., "A novel technique for removing *Wolbachia* infections from *Aedes albopictus*" (Diptera: Culicidae), J. Med. Entomol. 38, 844-849, 2001 (hereinafter Dobson et al., 2001) herein incorporated by reference.

Microinjection

Embryo injection was based upon techniques successfully used for mosquito transgenesis as taught by Morris, "Microinjection of mosquito embryos", In: Crampton, J. M., Beard, C. B., Loius, C. (Eds.), Molecular Biology of Insect Disease Vectors: A Methods Manual, Chapman & Hall, 423-429, 1997 (hereinafter Morris); Coates et al., "Mariner transposition and transformation of the yellow fever mosquito, *Aedes aegypti*", Proc. Natl. Acad. Sci. USA 95, 3748-3751, 1998 both herein incorporated by reference. Injection needles (Quartz with filament, O.D.: 1.0 mm, I.D.: 0.70 mm) were pulled with a P2000 micropipette puller (Sutter Instrument Co.; Novato, Calif.). Approximately ten blood-fed females (Hou or HT1) were held in *Drosophila* vials (Fisher Scientific) containing a wet filter paper funnel. HT1 embryos to be injected (recipient embryos) were collected after allowing females to oviposit for ≦90 min. Following a brief desiccation, gray embryos were aligned on double sided tape (Scotch 665; St. Paul, Minn.) and covered with halocarbon 700 oil (Sigma-Aldrich Co.). Donor Hou embryos were treated similarly but not desiccated. Cytoplasm was withdrawn from donor Hou embryos and injected into the posterior of recipient HT1 embryos using an IM300 microinjector (Narishige Scientific; Tokyo, Japan) as previously described by Morris. After injection, the embryos were incubated at 80% relative humidity and 27° C. for approximately 40 min. Embryos were then removed from oil and transferred to wet filter paper. Embryos were allowed to develop for 5 days on wet egg paper. Subsequently, the eggs were hatched ($G_0$) and reared using standard maintenance conditions as above.

Crosses of Transfected Lines

To ensure a compatible mating, $G_0$ females were isolated as virgins and mated with HT1 males. Following oviposition, $G_0$ females were assayed for *Wolbachia* infection using PCR. $G_0$ males were also PCR assayed for *Wolbachia* infection. $G_0$ females testing negative for *Wolbachia* infection were discarded along with their progeny. Infected $G_1$ females were sib mated, blood fed, isolated and allowed to oviposit. Following oviposition, $G_1$ females were PCR assayed for *Wolbachia* infection. $G_1$ females testing negative for *Wolbachia* infection were discarded along with their progeny. An introgressed line was generated by crossing wAlbB-infected females with UjuT males as previously described in Dobson et al., "Fitness advantage and cytoplasmic incompatibility in *Wolbachia* single- and superinfected *Aedes albopictus*", Heredity 93, 135-142, 2004, (hereinafter Dobson 2004). To determine CI levels, five virgin females were mated with five virgin males at $G_3$. Mated females were blood fed weekly using mice. Oviposition sites were available constantly to females, and oviposition paper was changed weekly. Hatch rates were scored 3 days after eggs were immersed into water. A majority of *Ae. albopictus* eggs hatch within a few hours of being submerged in deoxygenated water. Thus, delaying observations beyond 3 days would not affect estimates of egg hatch.

PCR Amplification

Ovaries or testis of adults were dissected and homogenized in 100 ul STE with 0.4 mg/ml proteinase K to extract DNAs previously described in accordance with O'Neill et al., "rRNA phylogenetic analysis of the bacterial endosymbionts associated with cytoplasmic incompatibility in insects", Proc. Natl. Acad. Sci. USA 89, 2699-2702, 1992 (hereinafter O'Neill 1992), incorporated herein by reference. General *Wolbachia* primers (81F-681R) and primers specific for the wAlbA (328F-691 R) and wAlbB (183F-691R) infections were used as previously described in Zhou et al., "Phylogeny and PCR-based classification of *Wolbachia* strains using wsp gene sequences", Proc. R. Soc. London B Biol. Sci. 265, 509-515, 1998 (hereinafter Zhou 1998), incorporated herein by reference.

Fluorescence In Situ Hybridization (FISH)

Dissected ovaries and oocytes were fixed for 15 min in freshly prepared 4% formaldehyde in PBS and then washed in PBS with 0.1% Tween 20. Hybridization was conducted following the manufacturers instruction (GeneDetect, Bradenton, Fla.) with buffer containing 200 ng probes at 37° C. overnight. Two FITC 50-end labeled 16s rDNA *Wolbachia* probes (synthesized by Sigma-Genosys Ltd., Haverhill, UK) were used with the sequence as following: [5'-ACCAGATA-GACGCCTTCGGCC-3'] (SEQ ID NO: 1) and [5'-CTTCT-GTGAGTACCGTCATTATC-3'] (SEQ ID NO: 2). Following hybridization, samples were washed at 45° C. and mounted on a glass slide with Vecta shield mounting media (Vector Laboratories; Burlingame, Calif.). Samples were viewed with Olympus IX70 fluorescence microscope and photographed using Magnafire software (Optronics; Goleta, Calif.).

Results of the Experiment

Figure 2:
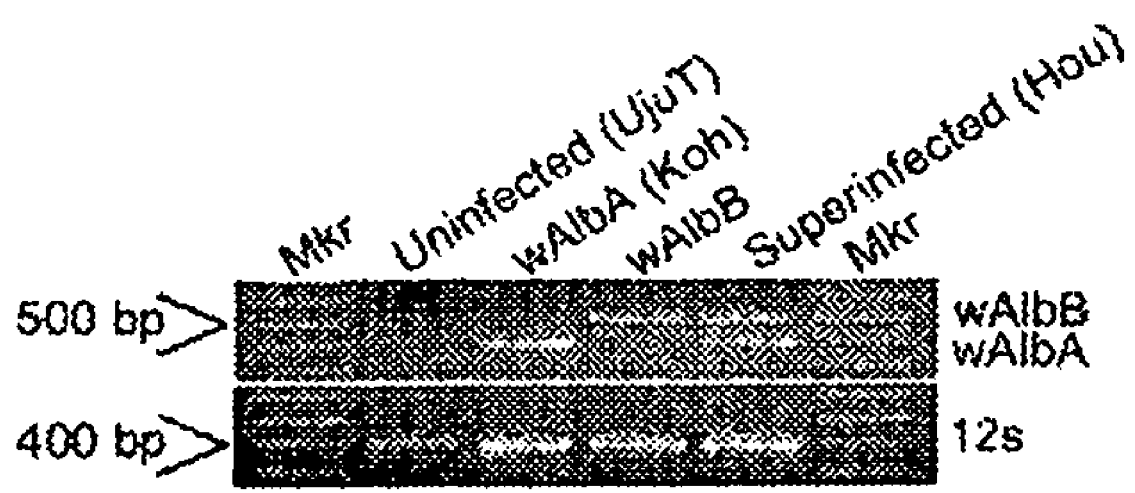
FIG. 2 is a PCR gel showing a strain-specific amplification of wAlbA and wAlbB *Wolbachia* type.

Cytoplasm from superinfected *Ae. albopictus* embryos (Hou) were microinjected into uninfected embryos (HT1). In one experiment, ten of 77 embryos ($G_0$) survived microinjection (12% hatch rate). Two of the resulting adults were female. Since males are a dead end host for *Wolbachia* infection, males were not used to establish lines. Instead, the eight adult males were sacrificed for PCR *Wolbachia* detection assays as shown in FIG. 2. Three males were PCR positive for both the wAlbA and wAlbB *Wolbachia* infection; two males were positive for only the wAlbB infection; *Wolbachia* was not detected in the remaining three males.

PCR tests of infected $G_0$ females showed one $G_0$ female to be positive for both the wAlbA and wAlbB infection. *Wolbachia* was not detected in the second $G_0$ female. Twenty-one $G_1$ isofemale lines were established from the infected $G_0$ female. $G_1$ PCR assays demonstrated 11 females to be positive for the wAlbB infection only. One $G_1$ female was positive for the wAlbA infection only. *Wolbachia* was not detected in the remaining nine $G_1$ females.

Three wAlbB-infected isofemale lines were established. Eggs from the wAlbA-infected $G_1$ female failed to hatch, and thus this line was lost. To determine the stability of *Wolbachia* infection in the wAlbB-transfected lines, PCR was repeated in subsequent generations. Consistent PCR detection of the infection continued through the generation immediately prior to submission of this article ($G_0$).

Figure 3:
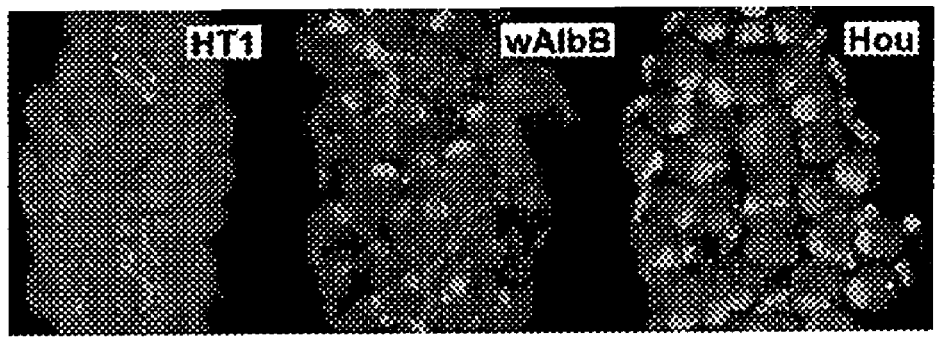
FIG. 3 is a micrograph in which panel (*a*) shows the distribution of *Wolbachia* in *Ae. albopictus* ovaries and panel (*b*) shows the distribution of *Wolbachia* in *Ae. albopictus* oocytes.
Figure 3:
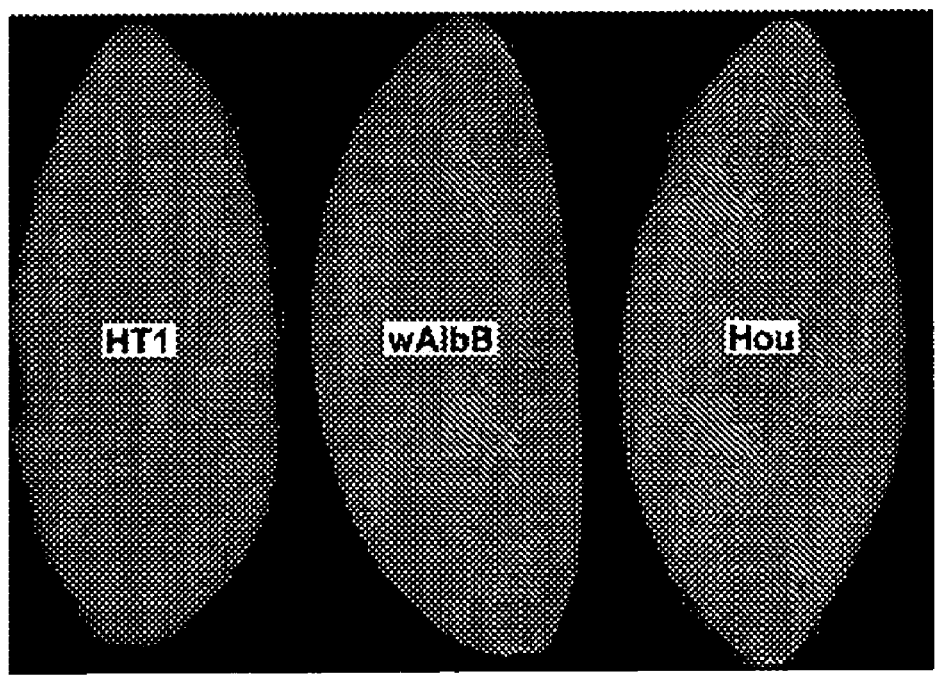

To characterize the distribution of *Wolbachia* in the transfected line, ovaries were dissected from $G_6$ females and examined. Hou and wAlbB oocytes displayed a similar pattern of *Wolbachia* staining at both embryonic poles, which was absent from uninfected oocytes as shown in FIG. 3. In FIG. 3, HT1 is an aposymbiotic (uninfected) strain; wAlbB is the transfected strain; and Hou is the naturally superinfected strain. A reduced level of *Wolbachia* was observed in ovaries of wAlbB females compared to ovaries of superinfected Hou females.

Crosses to characterize the CI pattern of the transfected wAlbB strain resulted in a low egg hatch rate in crosses of wAlbB males with either uninfected or wAlbA-infected females as summarized in Table 1. Crosses of the wAlbB males with superinfected females are compatible. Crosses of the wAlbB females with uninfected or wAlbB-infected males were compatible, although relatively low egg hatch rate (38.0%) was observed in the latter crosses as summarized in Table 1 below. CI persists over the lifetime of wAlbB females.

TABLE 1

Crosses of the transfected wAlbB line ($G_3$)

| Expected CI type | Cross[a] | Percent egg hatch[b] | Number of egg/ oviposition[b] | Oviposition number |
|---|---|---|---|---|
| Bidirectional CI | wAlbB × Koh | 3.6 ± 3.8 | 155 ± 55 | 13 |
|  | Koh × wAlbB | 2.4 74.4 | 162 ± 64 | 15 |
| Unidirectional CI | HT1 × wAlbB | 0.0 ± 0.0 | 170 ± 45 | 14 |
|  | wAlbB × Hou | 3.0 ± 2.1 | 150 ± 52 | 6 |
| Compatible | Hou × wAlbB | 73.8 ± 12.1 | 192 ± 60 | 15 |
|  | wAlbB × wAlbB | 38.0 ± 21.3 | 139 ± 48 | 6 |
|  | HT1 × HT1 | 90.9 ± 2.7 | 166 ± 139 | 3 |
|  | Koh × Koh | 88.0 ± 2.8 | 177 ± 85 | 4 |
|  | Hou × Hou | 82.5 ± 2.2 | 158 ± 57 | 4 |

[a]Female × male; HT1 is an aposymbiotic (uninfected) strain; wAlbB is the transfected strain; Koh is a wAlbA-infected strain; and Hou is the naturally superinfected strain
[b]Average ± standard deviation Egg hatch was observed to remain consistent in egg batches collected from the same females over a 4-week period as shown in FIGS. 4 (*a*) and 4 (*b*). The CI level was re-examined at $G_7$, resulting in similar results as $G_3$. Shown in FIGS. 4 (*a*) and 4 (*b*), crosses are female×male; HT1 is an aposymbiotic (uninfected) strain; wAlbB is the transfected strain; Koh is a wAlbA infected strain; and Hou is the naturally superinfected strain. Greater than 86% hatch resulted in crosses of wAlbB males with superinfected Hou females. No egg hatch was observed in crosses of wAlbB males and uninfected HT1 females.

To reduce potential inbreeding effects, one wAlbB line was introgressed with UjuT for three generations. As shown in FIG. 4 (*c*), the hatch rate in the introgressed strain increased to greater than 93%. The hatch rate observed in the un-introgressed wAlbB line also increased (72.8% in $G_7$; FIG. 4 (*c*)). Introgression did not affect CI. No egg hatch was observed in crosses of introgressed wAlbB males and uninfected HT1 females. Maternal inheritance rate was examined in the wAlbB line by screening 20 $G_6$ females using the PCR assay. *Wolbachia* infection was observed in all of the tested females. To examine for paternal transmission, rare progeny from incompatible crosses were reared to adult and then PCR assayed for infection type. Superinfection was not detected in the three progeny resulting from wAlbB×wAlbA and two progeny from wAlbA×wAlbB (female×male). The infection type in each of the progeny was consistent with expectations for maternal inheritance only (i.e., progeny infection type was the same as the maternal type).

*Wolbachia* in *Ae. albopictus* is known to represent a true superinfection (i.e., co-infection with two *Wolbachia* types) and not multiple copies of diagnostic genetic loci in a single *Wolbachia* type, based upon observations of the wAlbA single infection in mosquito lines and the wAlbB single infection in vitro. However, the wAlbB single infection has not been observed naturally. Surveys show that >99.4% of natural *Ae. albopictus* populations are superinfected. Furthermore, prior efforts to segregate the wAlbA and wAlbB infections using antibiotics were unsuccessful.

Based upon the genetic divergence of the wAlbA and wAlbB infections and prior crossing experiments, bidirectional incompatibility has been predicted for crosses between individuals single-infected with wAlbA and wAlbB. Here, crosses of the transfected wAlbB line were used to directly test predictions. Consistent with expectations for differing modification and rescue mechanisms, less than 4% egg hatch rate resulted in crosses between wAlbB males with either wAlbA or uninfected females as shown in Table 1. Crossing results demonstrate that the wAlbB infection is capable of inducing and rescuing the CI modification independent of the wAlbA infection. Crosses of wAlbB females with either wAlbA or superinfected males demonstrate that the wAlbB infection is unable to rescue the wAlbA modification. Although prior characterization of *Wolbachia* infections in other insects shows that CI levels can be affected by host age, the wAlbB infection in females is able to rescue modified sperm until female death as shown in FIGS. 4 (*a*)-4 (*c*).

Despite the observation that ovaries from the wAlbB line appeared to have lower infection levels relative to Hou ovaries (FIG. 3), the wAlbB infection was observed to be stably maintained in the transfected lines. PCR assays at $G_6$ suggest maternal inheritance in excess of 95%, consistent with prior characterization of naturally infected lines. *Wolbachia* specific staining showed a similar infection level and *Wolbachia* distribution in wAlbB and Hou oocytes (FIG. 3). Paternal transmission of *Wolbachia* infection provides a potential route for the evolution of superinfections. With paternal and maternal transmission, survivors of crosses between mates with different *Wolbachia* types would result in superinfected progeny. To examine for paternal transmission, the rare offspring from incompatible crosses between wAlbA and wAlbB strains were PCR tested. In each case, the *Wolbachia* infection was identical to the maternal infection type.

Low hatch rate (38.0%) was observed in compatible crosses of wAlbB individuals. Hypotheses to explain this observation include inbreeding effects associated with the establishment of isofemale lines (i.e., increased homozygosity of deleterious loci) and high mortality associated with the artificially generated single wAlbB infection type. The observed increase in egg hatch with introgression (FIG. 4 (c)) is consistent with predictions for an inbreeding effect. An increase in egg hatch was also observed in subsequent generations of a non-introgressed wAlbB line, reaching a plateau at approximately 70% (FIG. 4 (c)). Thus, the wAlbB single infection does not appear to be associated with increased mortality.

Although superinfection was detected in $G_0$ individuals surviving microinjection, only single infections were observed in $G_1$. It is useful to note that subsequent to $G_1$, maternal transmission loss was not observed.

The present method demonstrates a technique for *Wolbachia* transfection in *Ae. albopictus*. An ability to generate artificial *Wolbachia* infections and new CI crossing types represents an important advance toward implementation of proposed *Wolbachia*-based strategies for suppression and replacement of medically important mosquito vector populations. Thus the experiments described here demonstrate a successful transfection protocol.

For suppression strategies, injection of aposymbiotic *Ae. albopictus* can be used to generate strains that are bidirectionally incompatible with the superinfected field population. Injection of superinfected *Ae. albopictus* can be used to generate a triple-infected *Ae. albopictus* strain that is unidirectionally incompatible with superinfected field population.

Example 2

Transfecting *A. aegypti* by Microinjection with wAlbB *Wolbachia* Infection

*A. aegypti* were infected by embryonic microinjection with the wAlbB *Wolbachia* infection from *A. albopictus* in accordance with Xi and Dobson 2005. In brief, cytoplasm from *A. albopictus* eggs (Hou strain superinfected with wAlbA and wAlbB) was injected into *A. aegypti* eggs (Waco strain). *Wolbachia* were detected by polymerase chain reaction (PCR) as previously described in Dobson, et al., Genetics 160, 1087 (2002) (hereinafter Dobson 2002) and hereinafter incorporated by reference, in each of the five females ($G_0$) that survived from injection to adult. Only three females successfully produced progeny ($G_1$). PCR tests of $G_1$ individuals demonstrated the offspring of one female to be uninfected. The lines established from the remaining two females were only infected with the wAlbB, and one line (designated WB1) was selected for additional tests. In previous work on *A. albopictus*, wAlbB infections were obtained and not wAlbA in accordance with Xi and Dobson 2005. This may reflect the lower infection rate of wAlbA relative to wAlbB.

Figure 5:
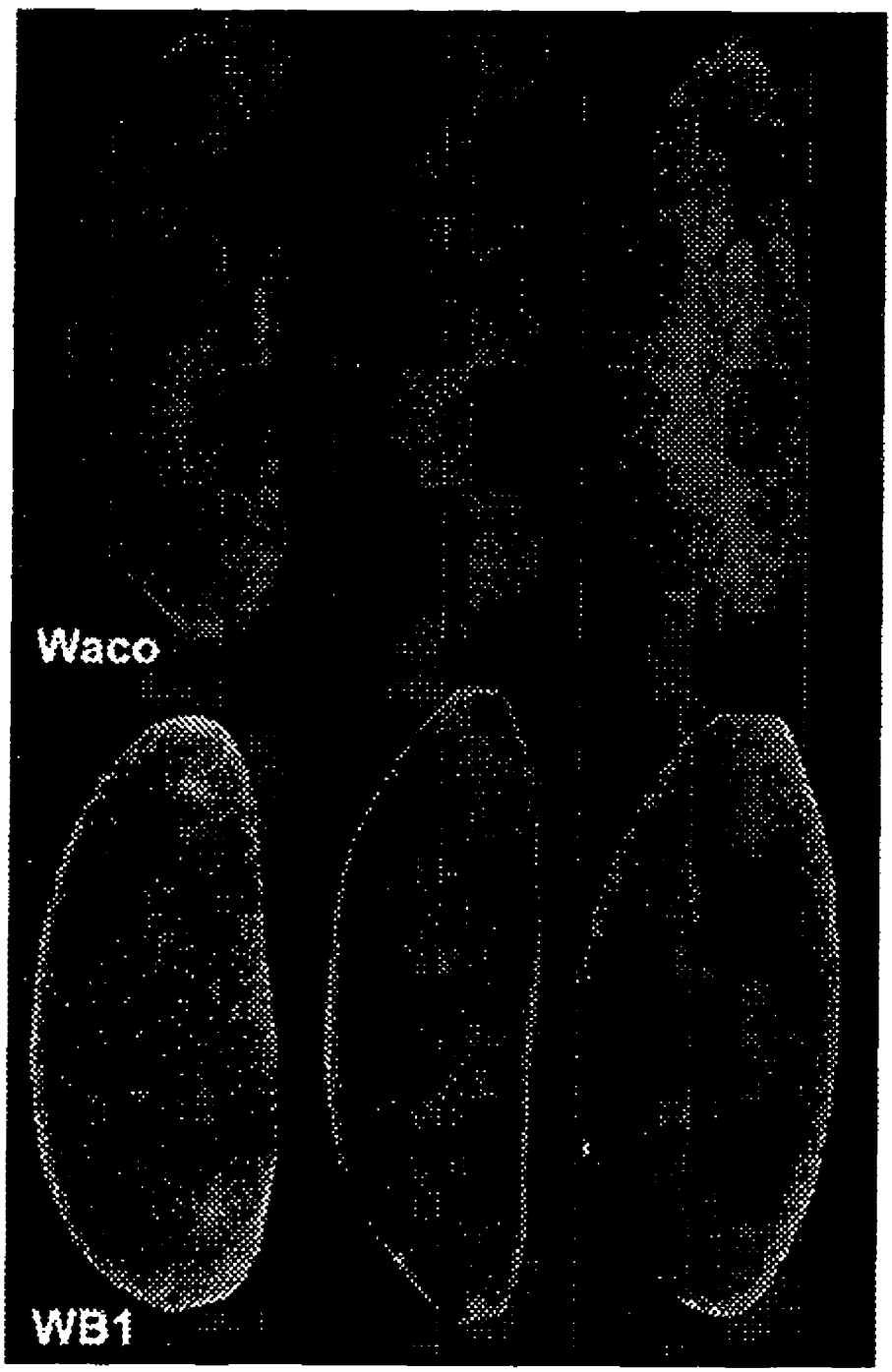
FIG. 5 is a micrograph of oocytes of uninfected Waco wAlbB-infected WB1 stained and a *Wolbachia*-specific FISH probe.

PCR assays of WB1 individuals in subsequent generations ($\leq G_{12}$) consistently identified *Wolbachia* infection. As a specific test of the maternal inheritance rate, progeny were collected from isolated WB1 females ($G_{12}$). After PCR confirmation of *Wolbachia* infection in 10 $G_{12}$ females, the progeny (10 daughters and 10 sons for each $G_{12}$ female) were assayed with PCR. All of the $G_{13}$ progeny (n=200) were infected by *Wolbachia* (95% binomial confidence interval between 0.9851 and 1.0). Fluorescence in situ hybridization (FISH) confirms high *Wolbachia* infection rates in WB1 oocytes (FIG. 5). The infection appears highest in the anterior, posterior, and cortical regions of oocytes, similar to the pattern observed in naturally infected *A. albopictus*.

Crosses were conducted to determine whether CI occurs as a result of the *Wolbachia* infection in the WB1 strain. The design of the cross experiment was as previously described in Dobson 2002. As shown in Table 2, the pattern of egg hatch resulting from crosses is consistent with strong CI, similar to that observed in *A. albopictus*, from which the wAlbB infection was derived. No egg hatch resulted from >3800 eggs examined from crosses of uninfected Waco females and infected WB1 males.

TABLE 2*

|  | Male Waco | Male WB1 |
| --- | --- | --- |
| Female Waco | 92.5 ± 3.7% (n = 9) | 0.0 ± .0.0% (n = 15) |
| Female WB1 | 69.1 ± 11.7% (n = 9) | 50.6 ± 12.9% (n = 15) |

*CI pattern resulting from crosses of the naturally uninfected Waco and the wAlb-transfected WB1 *A. aegypti* strains. Percent egg hatch ± standard deviation and number of cross replicates are shown for each of the four cross types. Crosses were conducted as described in Xi and Dobson (2005).

Among the compatible crosses, egg hatches resulting from WB1 crosses [51% and 69% (Table 2)] were significantly lower [Kruskal-Wallis, df (degrees of freedom)=1, P G 0.01] than the egg hatch observed in compatible crosses of Waco individuals (92%). Because the progeny of the WB1 $G_0$ female were sibling-mated during production of the WB1 isofemale line, the low egg hatch may reflect an inbreeding effect. Therefore, virgin WB1 females ($G_3$) were mated with uninfected Waco males. After the repeat of this introgression for six generations, the egg hatch increased to an average of 89% ($G_9$).

Strong CI and high maternal transmission rates suggest that wAlbB infection will invade an uninfected population. To test this prediction, WB1 females were released at different ratios into replicate Waco laboratory populations (FIG. 6 (a)). The population cage experimental design was as previously described in Dobson (2002). In the 20% initial release cage, the wAlbB infection frequency was observed to increase to 100% infection frequency within seven generations. Additional sampling in the eighth and ninth generations demonstrated that the infection frequency remained fixed at 100% (FIG. 6 (a)). Consistent with model predictions, a transient drop in egg hatch was observed during the cytotype replacement (circa generation four) (FIG. 6 (a)). The latter is expected owing to the frequent occurrence of CI crosses; however, once the infection becomes fixed within the population, CI crosses no longer occur, and the egg hatch rates recover.

Figure 6:
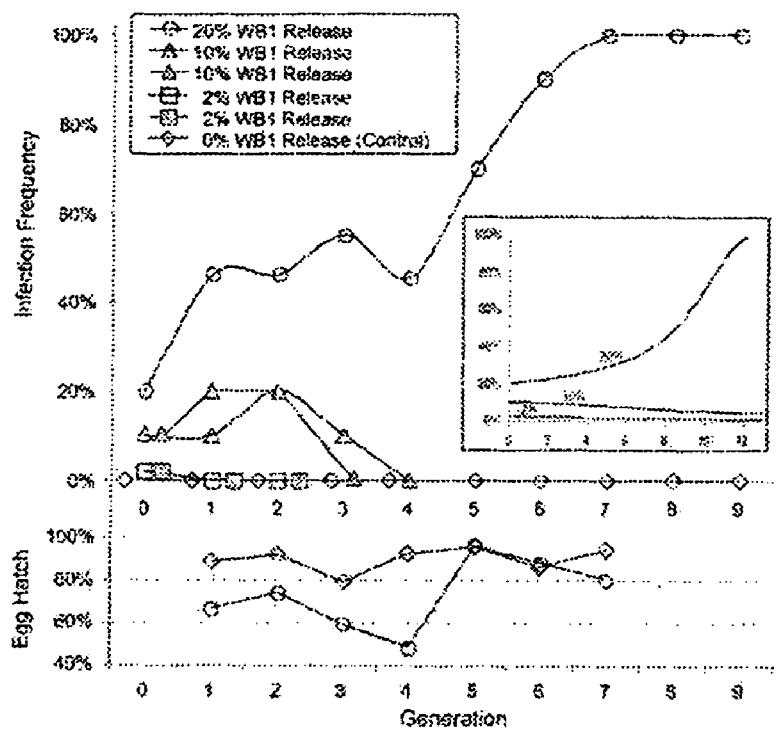
FIG. 6 (*a*) is a plot depicting *Wolbachia* infection frequency and FIG. 6 (*b*) is a plot depicting egg hatch rates after a single release of WB1 females into Waco populations, whereby the plots display model predictions of *Wolbachia* infection dynamics assuming complete CI, 100% material transmission and 15% fecundity cost associated with *Wolbachia* infection.
Figure 6:
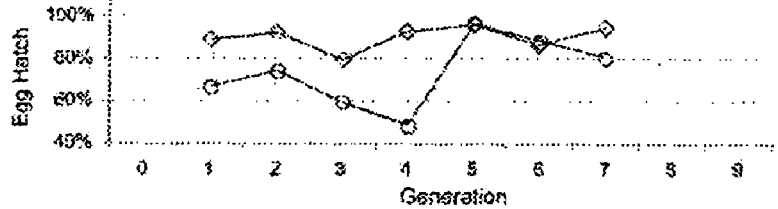

In cages established with an initial infection frequency of $\leq 10\%$, the infection was detected for up to four generations before its disappearance from the population (FIG. 6 (a)). Infection could not be detected in populations in cages initially infected at a rate of 2% release of WB1 females. Hence, the loss of *Wolbachia* infection from a population is predicted if the initial infection frequency is below a required threshold determined by CI level, fidelity of maternal transmission, and fitness costs associated with *Wolbachia* infection. Complete CI and no evidence of maternal transmission failure were observed in this study. If no fitness costs were associated with the infection, one would predict *Wolbachia* invasion in all cages in which WB1 females were released. However, a threshold infection frequency of ~20% was estimated which provides evidence of there is a substantial fitness cost associated with wAlbB infection in *A. aegypti*. By using a previously developed model, an approximate 15% fecundity cost was estimated to be associated with the wAlbB infection on the basis of the observed population replacement events (FIG. 6 (a)).

An analysis of fecundity costs associated with the wAlbB infection neither revealed any differences in egg number (P>0.3, t test) in comparisons of WB1 females (57.8±17.6 eggs per female, n=12) with Waco females (52.4±8.5 eggs per female, n=14) nor revealed any differences in egg hatch rate between Waco and WB1 strains ($X^2$ test, df 0 1, P>0.05).

The present method provides the ability to artificially infect *A. aegypti* with wAlbB where *A. aegypti* is a major disease vector, and thus represents an important step toward proposed population replacement strategies. The observed high CI rates, high maternal inheritance, and ability of wAlbB to invade an uninfected laboratory population to infection fixation represent desired characteristics for population replacement strategies.

Example 3

The Transfer of *Wolbachia* from *Drosophila* Stimulants into the Invasive Pest and Disease Vector: *Aedes albopictus* (Asian Tiger Mosquito)

The following example demonstrates the maintenance of infection in a transfected mosquito strain (HTR), displaying an ability to induce cytoplasmic incompatibility and maternal transmission rates similar to that observed in D stimulants. The HTR strain is bidirectionally incompatible with naturally infected *Ae. albopictus*, allowing for the use of HTR to suppress field populations. An initial laboratory test of the latter suppression strategy, demonstrates that HTR male releases into naturally infected *Ae. albopictus* populations results in reduced egg hatch.

This example generates an artificial *Wolbachia* infection useful for *Ae. albopictus* suppression. *Ae. albopictus* was selected due to its importance as a pest and disease vector, the ability of *Ae. albopictus* to naturally support *Wolbachia* infection (unlike *Ae. aegypti* and *Anopheles* sop., which are not naturally infected), and the previously developed microinjection technique as taught in Xi and Dobson 2005.

The results demonstrate that the wRi infection has been successfully transferred from *Drosophilia* into *Ae. albopictus* and is stably maintained in the transfected line (HTR). The HTR line displays a unique CI pattern and is bidirectionally incompatible with both natural infections and the previously generated artificial infection as taught by Xi and Dobson 2005. Initial suppression trails show that releases of HTR males into laboratory cages of superinfected populations result in reduced egg hatch.

Individuals with the *Ae. albopictus* Houston (Hou) strain are naturally superinfected with both the wAlbB and wAlbA *Wolbachia* types in accordance with Sinkins, S. P., Brig, H. R. & O'Neil, S. L. (1995) "*Wolbachia* superinfections and the expression of cytoplasmic incompatibility" Proc R Soc Lund [Boil] 261, 325-330, herein incorporated by reference. The aposymbiotic HT1 strain was generated by tetracycline treatment of the Hou strain. The Koh Samui strain (Koh) is naturally single infected with the wAlbA *Wolbachia* type. The HOB strain is single infected with wAlbB and was artificially generated via microinjection of HT1 with Hou cytoplasm in accordance with Xi and Dobson 2005. *D. stimulants* Riverside (DSL) are naturally infected with the wRi infection. Mosquito and *Drosophilia* strains were maintained following standard procedures as described previously in Roberts, D. B. (1998) *Drosophila*: a practical approach (GIRL Press at Oxford University Press, Oxford) and Dobson, S. L., Marshland, E. J. & Rattanadechakul W. (2001) "*Wolbachia*-induced cytoplasmic incompatibility in singe- and superinfected *Aedes albopictus*." J. Med. Entomol. 38, 382-387, (hereinafter Dobson et al. 2001), both herein incorporated by reference.

Embryo injection was based upon techniques successfully used for mosquito and *Drosophilia* transfection in accordance with Xi, Z., & Dobson, SAL., 2005, "Characterization of *Wolbachia* transfection efficiency by using microinjection of embryonic cytoplasm and embryo homogenate" *Appl Environ Microbiol.*, 71, 3199-3204, (hereinafter Xi et al. 2005) and Xi and Dobson 2005. Microinjection needles were prepared from quartz microcapilaries (#QF100-70-7.5; Sutter Instrument Co., Novato, Calif.) using a P2000 micropipette puller (Sutter Instrument Co., Novata, Calif.).

DSR embryos were used as the donor of wRi infected cytoplasm. DSR embryos were collected ≦30 min post oviposition using apple juice agar plates with yeast paste. Embryos were dechorionated in 50% bleach for 2 minutes, rinsed, aligned on agar plate and transferred onto a glass slide with double stick tape, and covered with water saturated halocarbon 700 oil (Sigma-Aldrich Co.). Donor DSR embryos were not desiccated.

HT1 embryos (recipient embryos) were aligned on wet filter paper, transferred onto a cover slip with double sided tape (Scotch 665; St. Paul, Minn.), briefly desiccated, and covered with water saturated halocarbon 700 oil. Embryos were injected ≦90 minutes post oviposition.

Cytoplasm was withdrawn from the posterior of donor DSR embryos and injected into the posterior of recipient HT1 embryos using an IM300 microinjector (Narishige Scientific; Tokyo, Japan) similar to prior descriptions of Xi et al. 2005 and Xi and Dobson 2005.

Following injection, HT1 embryos were incubated at 80% relative humidity and 27° C. for approximately 40 minutes. Subsequently, the embryos were removed from the oil and transferred onto wet filter paper, where they were allowed to develop for five days. The eggs were then submerged in deoxygenated water to hatch. Resulting larvae ($G_0$) were reared using standard conditions as described above.

Enclosing $G_0$ females were isolated as pupae to assure virginity and were subsequently mated with HT1 males. Following blood feeding and oviposition, $G_0$ females were assayed for *Wolbachia* infection via PCR (described below). $G_0$ males were assayed for *Wolbachia* infection approximately two days post eclosion. $G_0$ females testing negative for *Wolbachia* infection were discarded along with their progeny. One wRi infected line was selected for subsequent experiments and designated as the "HTR" strain: Houston strain, Tetracycline treated, with wRi infection. HTR individuals were sibling mated in the $G_1$ and $G_2$. Beginning in $G_3$, 50 virgin HTR females were out crossed with 50 HT1 males in every generation.

Crosses were conducted to characterize the pattern of CI and egg hatch rates resulting from crosses between HTR individuals and individuals with differing *Wolbachia* infection types. In all crosses, ten virgin females were mated with ten males. All individuals were <5 days old when crossed. Subsequently, females were blood fed and provided with oviposition cups.

For PCR assays, DNA was extracted from adult ovaries or testis via homogenization in 100 μl STE with 0.4 mg/ml proteinase K as previously described in O'Neill, S. L., Giordano, R., Colbert, A. M., Karr, T. L., & Robertson, H. M., 1992, 16S "rRNA phylogenetic analysis of the bacterial endosymbionts associated with cytoplasmic incompatibility in insects" *PNAS* 89, 2699-2702, (hereinafter O'Neill), herein incorporated by reference. Presence of *Wolbachia* was detected using general *Wolbachia* primers (81F, 691R) as taught in Zhou, W., Rousset, F., & O'Neill, S. L., 1998, "Phylogeny and PCR based classification of *Wolbachia* strains using wsp gene sequences" Proc R Soc Lond Biol. 265, 509-515, (hereinafter Zhou et al.). *Wolbachia* infection type was determined using primers specific for the wAlbA (328F, 691 R), wAlbB (183F, 691R) and wRi (169F, 569R) infections in accordance with Zhou et al. and Kang, L., Ma, X., Cai, L., Liao, S., Sun, L., Zhu, H., Chen, X., Shen, D., Zhao, S., & Li, C., 2003, "Superinfection of *Laodelphax striatellus* with *Wolbachia* from *Drosophila simulans*" Heredity 90, 71-76, herein incorporated by reference. As additional confirmation of infection type, primers specific for a prophage sequence (phgWOf, phgWOr) were used. The latter primers result in a PCR amplification product with wRi but not with wAlbA or wAlbB infections in Hou. For mosquitoes failing to amplify the above primers (e.g. HT1), template quality was confirmed using 12S mitochondrial primers as previously disclosed in O'Neill. For FISH, oocytes were dissected from females four days after blood feeding and were fixed for 15 min in freshly prepared 4% formaldehyde in PBS and then FISH stained as described previously in Xi and Dobson 2005. For the maternal transmission assay, twenty HTR $G_5$ females and eleven HTR $G_6$ females were randomly selected and PCR assayed. Progeny ($G_7$) from one infected HTR $G_6$ female were reared to adult and PCR tested. In each generation, the maternal transmission efficiency was estimated using the percentage of PCR positive individuals among those tested.

All mosquitoes used in suppression cage tests were isolated as pupae to assure virginity. Fifty Hou females and ten Hou males were present in all of the cages. The number of HTR males ($G_5$) was varied between cages. Male Hou:HTR ratios were: 10:500, 10:100, 10:20, and 10:0. All males were <1 week post eclosion. One day after adding males to cages, fifty Hou females (<1 week past eclosion) were added to each cage. Prior to adding females, cages were examined to assure that minimal male mortality had occurred. Mating was observed immediately upon addition of females to cages. Following blood feeding, females were allowed to oviposit for one week. Egg hatch rates were determined as described above.

Cytoplasm from wRi infected *D. simulans* Riverside embryos was microinjected into aposymbiotic HT1 *Ae. albopictus* embryos. A total of 695 HT1 eggs were injected in three experiments, resulting in 15 $G_0$ females that survived to adult summarized in Table 3. PCR assays were conducted to diagnose *Wolbachia* infection in $G_0$ adults. As shown in Table 3, *Wolbachia* infection was detected in 33% of surviving $G_0$ females and 40% of surviving $G_0$ males.

TABLE 3

Survival of microinjected Ae. albopictus embryos, and the resulting Wolbachia infection status in the $G_0$ individuals surviving to adult.

| | Percent Survival | | | | $G_0$ Infection Status (Infected/total) | |
|---|---|---|---|---|---|---|
| Experiment | Hatch (Larvae/ eggs) | Pupation (Pupae/ larvae) | Eclosion (Adult/ pupae) | Sex ratio (Female/ male) | ♀ | ♂ |
| 1 | 3.4% (8/233) | 75.0% (6/8) | 83.3% (5/6) | 100.0% (5/5) | 40.0% (2/5) | (0/0) |
| 2 | 1.9% (6/316) | 50.0% (3/6) | 100.0% (3/3) | 66.7% (2/3) | 0% (0/2) | 0% (0/1) |
| 3 | 15.8% (23/146) | 78.3% (18/23) | 66.7% (12/18) | 66.7% (8/12) | 37.5% (3/8) | 50% (2/4) |

Of the five PCR positive $G_0$ females, only one female produced hatching eggs. The remaining $G_0$ females either failed to oviposit or their eggs failed to hatch. Three daughter ($G_1$) resulting from the PCR positive $G_0$ female were sib mated, blood fed, isolated and allowed to oviposit. Following oviposition, the $G_1$ females were PCR assayed for *Wolbachia* infection similar to $G_0$ females. Each of the three G1 females tested positive for *Wolbachia* infection. One of the latter isofemale lines was randomly selected for subsequent experiments and designated as the HTR strain. Subsequently, PCR assays of HTR individuals have consistently detected *Wolbachia* infection through $G_9$.

As an initial characterization of the maternal transmission rate, HTR females were examined at $G_5$, $G_6$ and $G_7$. At $G_5$, 20 females were randomly selected and PCR assayed for *Wolbachia* infection. *Wolbachia* amplification products were observed in 90% of the females. A repeat of this experiment at $G_6$ observed 11/11 (100%) females to be infected. The progeny ($G_7$) from one of the infected $G_6$ females were reared to adult and PCR tested. In the latter test, PCR amplification products were observed in 18/20 (90%) of the assayed $G_7$ females.

Figure 7:
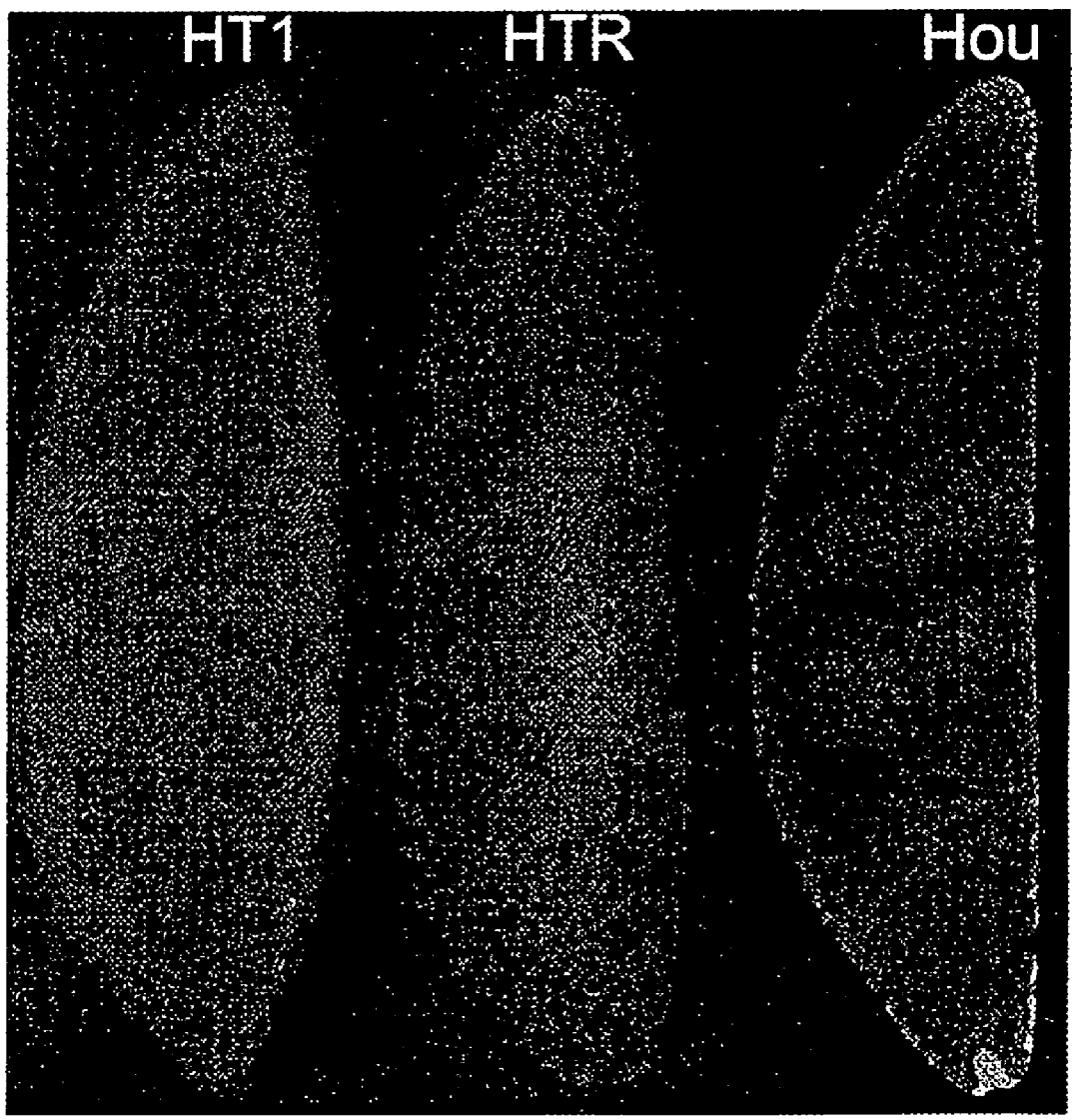
FIG. 7 is a micrograph showing *Wolbachia* distribution in oocytes of naturally superinfected (Hou) aposymbiotic (HT1) and wRi tranfected HTR strain.

Fluorescent in situ hybridization (FISH) was used to examine the distribution of *Wolbachia* in transfected HTR oocytes. *Wolbachia* localization in HTR oocytes was observed to differ from that observed in naturally superinfected Hou oocytes as shown in FIG. 7. *Wolbachia* was observed to be concentrated towards the center of HTR oocytes. In contract, the anterior and posterior is the focus of infection in naturally infected Hou oocytes and the transfected HTB strains.

Figure 8:
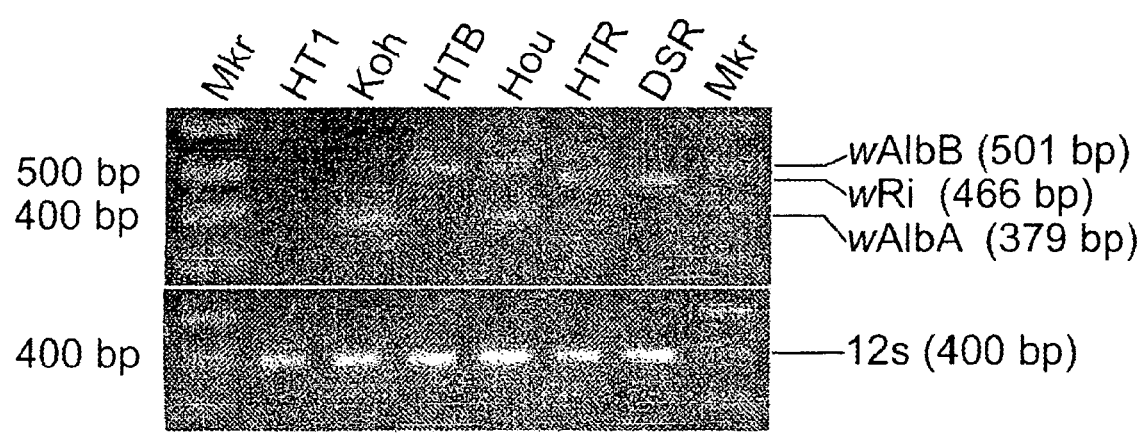
FIG. 8 is a PCR gel showing a diagnostic pattern of amplification products resulting with *Wolbachia* specific PCR primers where the depicted gel illustrates all of the amplification products that result when each *Ae. albopictus* strain is amplified with all four primer sets.

To determine the type of *Wolbachia* infection present in HTR, diagnostic PCR primers were used as shown in FIG. 8. Consistent with expectations for host insects infected with the wRi infection only, PCR assays of the HTR and DSR individuals result in amplification products of the expected size using the 169F/569R primer set, but not with the 328F/691R primer sets. The 169F/569R primer set did not amplify any of the other *Ae. albopictus* strains. As an additional confirmation of *Wolbachia* type, DNA from each of the *Ae. albopictus* strains and DSR flies was amplified using the phgWOf/phgWOr primer set. The latter amplification was similar to the 169F/569R primer set in that amplification products were only obtained from HTR and DSR. The Koh and HTB strains amplify with the 328F/691 R or 183F/691R primer sets. The HT1 strain does not amplify with the *Wolbachia*-specific primers.

Given that the wRi causes CI in its natural *D. simulans* host, crosses between HTR and HT1 were conducted to determine the CI pattern relative to the other *Ae. albopictus*. Additional crosses were conducted to determine the CI pattern relative to other *Ae. albopictus* infections (i.e. the wAlbA single infection, the wAlbB single infection, and the superinfection). As shown in Table 4, crosses of HTR individuals with the other infection types resulted in a unique pattern of CI. Specifically, a typical pattern of unidirectional CI was observed in crosses between HTR with uninfected HT1 individuals. Bidirectional CI was observed in crosses of HTR with single-infected (Koh, HTB) and superinfected (Hou) individuals.

TABLE 4

Egg hatch resulting from crosses of the transfected HTR line ($G_3$)

| Expected CI Type | Cross* | Infection Type | | Percent Egg Hatch[+] | Eggs scored |
|---|---|---|---|---|---|
| | | Female | Male | | |
| Bidirectional CI | Koh × HTR | wAlbA | wRi | 5.9 ± 4.8% | 2119 |
| | HTR × Koh | wRi | wAlbA | 2.8 ± 1.5% | 2040 |
| | HTB × HTR | wAlbB | wRi | 9.9 ± 5.4% | 1434 |
| | HTR × HTB | wRi | wAlbB | 0.3 ± 0.5% | 2152 |
| | Hou × HTR | wAlbA, wAlbB | wRi | 14.2 ± 6.6% | 2972 |
| | HTR × Hou | wRi | wAlbA, wAlbB | 0.4 ± 0.4% | 3216 |

TABLE 4-continued

Egg hatch resulting from crosses of the transfected HTR line (G₃)

| Expected CI Type | Cross* | Infection Type Female | Infection Type Male | Percent Egg Hatch⁺ | Eggs scored |
|---|---|---|---|---|---|
| Uni-directional CI | HT1 × HTR | — | wRi | 3.8 ± 3.3% | 1916 |
| | HTR × HT1 | wRi | — | 75.5 ± 9.7% | 2157 |
| Compatible | HTR × HTR | wRi | wRi | 57.1 ± 10.5% | 2136 |
| | Koh × Koh | wAlbA | wAlbA | 81.0 ± 4.6% | 635 |
| | HT1 × HT1 | — | — | 80.8 ± 0.3 | 1159 |
| | Hou × Hou | wAlbA, wAlbB | wAlbA, wAlbB | 82.6 ± 2.7 | 1883 |

*Female × Male
⁺Average ± Standard Deviation

The ability of the wRi infection in the HTR to induce CI was measured as the level of egg hatch resulting from crosses of HTR males with females differeing in their infection type. The strongest CI (<4% egg hatch) was observed in crosses with uninfected HT1 females. A similar CI level (~6% hatch) was observed in crosses with wAlbA infected Koh females. In contrast, higher egg hatch levels were observed in crosses with wAlbB infected HTB females and superinfected Hou females (9.9% and 14.4% hatch rate, respectively). Reciprocal crosses were conducted to examine the ability of wRi to rescue CI caused by other infection types. Low egg hatch (<3%) was observed in crosses of HTR females with males harboring different *Wolbachia* types. Consistent with expectations for *Wolbachia* induced CI, HTR females are compatible with both HTR males and uninfected males.

The egg hatch resulting from the HTR×HTR cross was significantly lower than the other compatible crosses, including the HTR×HT1 (female×male; Chi-square test, P<0.0001) and compatible crosses of Koh, HT1 and Hou (Chi-square test, P<0.05). To reduce possible inbreeding depression effects associated with the use of isofemale lines in generating the HTR strain, HTR females were repeatedly out crossed to HT1 males beginning in $G_3$. The HTR egg hatch was observed to increase from 58% hatch in $G_3$ to: 77% in $G_4$, 85% in $G_6$, and 92% in $G_8$.

Figure 9:
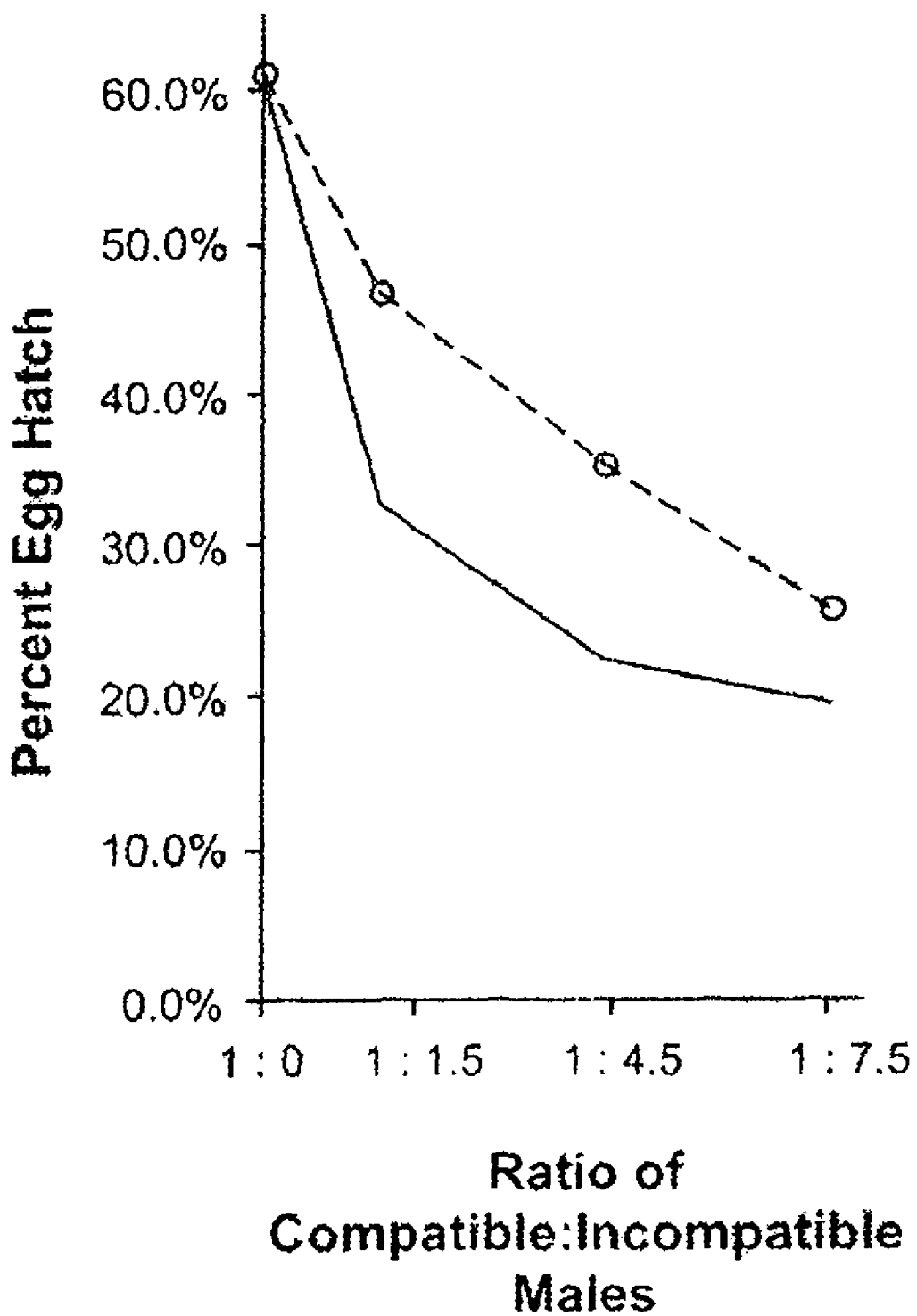
FIG. 9 is a graph depicting suppression of egg hatch in populations of naturally super-infected *Ae. albopictus* (Hou) via release of transfected HTR males.

The bidirectional CI observed between HTR and the naturally superinfected Hou strain suggests a strategy for suppressing *Ae. albopictus* populations via releases of HTR males. As an initial test of this strategy, cages were established with varying rations of HTR:Hou males. As shown in FIG. 9, the observed egg hatch decreases with an increasing ratio of HTR males in the population.

The present experiment demonstrates the embryonic microinjection can be used to establish a novel *Wolbachia* infection in a medically important mosquito. FISH staining shows that the wRi infection in transfected *Ae. albopictus* females (HTR) is transmitted to offspring during oogenesis. PCR assays demonstrate the HTR infection to be stable, with >90% infection frequency throughout the nine mosquito generations encompassed by this report. The wRi infection is able to induce CI in the transfected HTR strain and displays a unique pattern of CI relative to other infections in *Ae. albopictus*.

Relative to other CI crosses of HTR males, higher egg hatch is observed when wRi infected males are mated with females infected with wAlbB (Chi-square test, P<0.01), including both HTB and Hou females. Interestingly, a similar pattern was observed in a prior transfection study examining the interaction between *Ae. albopictus* infections and wRi in *D. simulans*. In the prior study, egg hatch resulting from crosses of females infected with *Ae. albopictus Wolbachia* and wRi males was approximately 10% higher than the reciprocal cross. However, the prior study did not determine the specific infection type(s) transfected from *Ae. albopictus* (Hou strain) into *D. simulans*.

The observed pattern of wRi distribution in *Ae. albopictus* oocytes is distinct from that of natural infections described in *Aedes* and *Culex*. The wAlbA, wAlbB, and wPip infections are concentrated at the oocyte poles of *Ae. albopictus* and *Cx. pipiens*. In contrast, the wRi infection is concentrated in the oocyte center (FIG. 7). The wRi distribution in HTR also differs from that reported in natural and transfected *Drosophilia* hosts, where in concentrates in the cortical region of oocytes. The unusual distribution of wRi in HTR oocytes is consistent with a prior report showing the *Wolbachia* embryonic distribution can be affected by host type.

The pattern of bidirectional CI observed in crosses between HTR and Hou provides evidence that the HTR strain can be useful for the suppression of naturally superinfected *Ae. albopictus* populations. Specifically, releases of HTR males (mosquito males do not blood feed or transmit disease) would induce CI and reduce egg hatch when mating with naturally superinfected females occurring in the field. Initial tests demonstrate that HTR male releases suppress egg hatch in the targeted laboratory cage population and that greater suppression results as the ratio of incompatible males increase. The initial results are encouraging, and demonstrate the need for additional studies examining the applied use of HTR male releases for suppressing field populations of *Ae. albopictus*.

The results demonstrate that HTR male releases can suppress egg hatch in naturally infected *Ae. albopictus* populations. Imperfect CI and maternal transmission failure is observed with HTR, resulting in ~14% egg hatch in crosses of Hou females and HTR males. Thus, continued releases of HTR males into a naturally superinfected population would be expected to reduce egg hatch and the bidirectionally incompatible strain generated can be useful for applied suppression strategies, in natural *Ae. albopictus* populations.

It will now be apparent to one of ordinary skill in the art that the present invention provides advantageous features not found in the art. Included is the ability to now suppress a mosquito population using males that are artificially infected with *Wolbachia*.

Although the aforementioned examples are directed to *Aedes* mosquitoes, the same techniques can be applied to other mosquito species including those of the genera *Culex* and *Anopheles*.

Prior transfection experiments demonstrate that the microinjection technique can be used to successfully establish artificial *Wolbachia* infections in both mosquitoes that are naturally infected and mosquitoes that are naturally uninfected. Furthermore, prior experiments show an ability to transfer *Wolbachia* infections between different insect species, including intraspecific and interspecific transfers between mosquitoes (Diptera: Culicidae) and transfers between different insect Families (i.e., from Drosophilidae to Culicidae). Embryonic microinjection techniques have been used previously with *Culex* and *Anopheles* species to accomplish genetic transformation. Thus, the latter mosquito species are expected to survive the microinjection approach directed at the transfer of *Wolbachia* infections. Thus, the microinjection approach described above in the Examples is applicable with naturally infected and naturally uninfected mosquitoes within other mosquito species, including the *Culex* and *Anopheles* genera.

What is claimed is:

1. An artificial bacteria infected mosquito species selected from the subfamilies Anophelinae and Culicinae, said mosquito infected with one or more *Wolbachia* species which does not naturally infect the mosquito species, wherein cytoplasm of infected mosquito embryo is microinjected into target mosquito embryo to generate the artificial bacteria infected mosquito, wherein when an infected male mosquito is crossed with an uninfected female mosquito or a female mosquito with a different infection type, a reduced number of offspring will be generated, and when an infected female is crossed with an uninfected male or a male infected with a similar infection, infected offspring will be generated, and wherein the mosquito species is medically important.

2. The artificial bacteria of claim 1, wherein said mosquito is selected from the genera consisting of *Aedes, Culex* and *Anopheles*.

3. The mosquito species of claim 1, wherein the mosquito species is an *Aedes* mosquito species selected from the group consisting of *Aedes albopictus, Aedes aegypti* and *Aedes polynesiensis*.

4. The mosquito species of claim 3, wherein said *Aedes* mosquito is *Aedes albopictus* and said *Wolbachia* is selected from the group consisting of wAlbB, wRi and wMelPop.

5. The mosquito species of claim 3, wherein said *Aedes* mosquito is *Aedes albopictus* and said mosquito is triply infected with wAlbA+wAlbB+wRi.

6. The mosquito species of claim 3, wherein said *Aedes* mosquito is *Aedes aegypti* and said bacteria is wAlbB.

7. The mosquito species of claim 3, wherein said *Aedes* mosquito is *Aedes polynesiensis* and said *Wolbachia* is wCon.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: probe sequence

<400> SEQUENCE: 1
accagataga cgccttcggc c                                          21

<210> SEQ ID NO 2
<211> LENGTH: 23
<212> TYPE: DNA
<213> ORGANISM: Artificial
<220> FEATURE:
<223> OTHER INFORMATION: probe

<400> SEQUENCE: 2
cttctgtgag taccgtcatt atc                                        23